United States Patent
Otiai et al.

(10) Patent No.: US 6,703,468 B1
(45) Date of Patent: Mar. 9, 2004

(54) COMPOUND, POLYMER PREPARED FROM THE COMPOUND, AND COMPOSITION COMPRISING THE POLYMER

(75) Inventors: Michi Otiai, Yokohama (JP); Takao Hattori, Yokohama (JP); Yoshio Kitada, Yokohama (JP); Hideo Kuroda, Yokohama (JP); Midori Oyobikawa, Yokohama (JP); Satoshi Ichinomiya, Yokohama (JP)

(73) Assignee: Pola Chemical Industries Inc., Shizuoka (JP)

( * ) Notice: Subject to any disclaimer, the term of this patent is extended or adjusted under 35 U.S.C. 154(b) by 0 days.

(21) Appl. No.: 09/857,505

(22) PCT Filed: Dec. 2, 1999

(86) PCT No.: PCT/JP99/06772

§ 371 (c)(1),
(2), (4) Date: Aug. 20, 2001

(87) PCT Pub. No.: WO00/32560

PCT Pub. Date: Jun. 8, 2000

(30) Foreign Application Priority Data

| Dec. 3, 1998 | (JP) | 10-360042 |
| Feb. 12, 1999 | (JP) | 11-033628 |
| Feb. 12, 1999 | (JP) | 11-033728 |
| Apr. 2, 1999 | (JP) | 11-096243 |
| Aug. 30, 1999 | (JP) | 11-242779 |

(51) Int. Cl.⁷ ............................................. C08F 226/02
(52) U.S. Cl. .................... 526/307.6; 526/288; 526/304; 526/307; 526/312; 526/318.3
(58) Field of Search ................................ 526/288, 304, 526/307, 317.6, 312, 318.3; 424/401

(56) References Cited

U.S. PATENT DOCUMENTS

| 4,495,361 A | 1/1985 | Friends et al. |
| 4,687,732 A | 8/1987 | Ward et al. |
| 4,839,166 A | 6/1989 | Grollier et al. |
| 4,844,889 A | 7/1989 | Papantoniou et al. |
| 5,133,970 A | 7/1992 | Petereit et al. |
| 5,369,142 A | 11/1994 | Culbertson et al. |
| 5,478,919 A | * 12/1995 | Koskan et al. ............. 528/363 |
| 5,723,133 A | * 3/1998 | Nagai et al. ................. 424/401 |
| 5,939,078 A | * 8/1999 | Fujimura et al. ........... 424/401 |
| 6,348,200 B1 | * 2/2002 | Nakajima et al. .......... 424/401 |

FOREIGN PATENT DOCUMENTS

| EP | 0 761 604 A2 | 3/1997 |
| GB | 1 466 150 | 3/1977 |
| GB | 1 541 670 | 3/1979 |
| JP | 48-11469 | 9/1974 |
| JP | 04213311 | 8/1992 |
| JP | 05-070321 | 3/1993 |
| JP | 07-207037 | 8/1995 |
| JP | 08-157815 | 6/1996 |
| WO | WO 96/27363 | 9/1996 |
| WO | WO97/38969 | 10/1997 |

OTHER PUBLICATIONS

Syntheses of Photosensitive Poly (amino acids), Masato Nanasawa, et al., Bulletin of the Chemical Society of Japan, vol. 48 (9), pp. 2588–2591, 1975.
Stability Constants of N–Isobutyroyl–L–Lysine and Poly(N–Methacryloyl–L–Lysine) Complexes, A. Lekchiri, et al., Polyhedron vol. 6, No. 3, pp. 633–639, 1997.
L–Lysin– and Poly–L–Lysin–Containing Polymer Hydrogel Sorbents, V.V. Chupov, et al. Vysokomol. Soedin., Ser. A, 1992, vol. 34, No. 2, pp 20–28.
A Mechanistic Study of the Hydrolytic Stability of Poly(2–(dimethylamino)ethyl methacrylate), P. van de Wetering, et al. 1998 American Chemicl Society, 31, 8063–8068.

* cited by examiner

*Primary Examiner*—Helen L. Pezzuto
(74) *Attorney, Agent, or Firm*—Knobbe, Martens, Olson & Bear LLP

(57) ABSTRACT

A composition comprising a polymer containing a compound represented by Formula (1) or a salt thereof as a constituent monomer, or a polymer containing a structure represented by Formula (9) as a partial structure is used for protecting or improving skin.

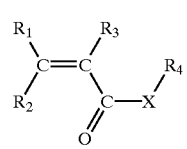

Formula (1)

In the formula, R1, R2 and R3 each independently represent hydrogen atom, an alkyl group, an alkoxyl group, or an alkylamino group; R4 represents an amino acid residue, a polyamine residue, or an aminoalcohol residue; and X represents oxygen atom or a group represented as NH.

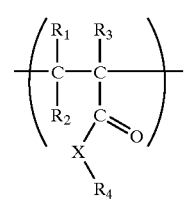

Formula (9)

In the formula, R1, R2 and R3 each independently represent hydrogen atom, an alkyl group, an alkoxyl group, or an alkylamino group; R4 represents an amino acid residue, a polyamine residue, or an aminoalcohol residue; and X represents oxygen atom or a group represented as NH.

16 Claims, 1 Drawing Sheet

COMPOUND, POLYMER PREPARED FROM THE COMPOUND, AND COMPOSITION COMPRISING THE POLYMER

This is the U.S. National Phase under 35 U.S.C. §371 of International Application PCT/JP99/06772, filed Dec. 2, 1999, which clams priority of JP 10/360042, filed Dec. 3, 1998.

TECHNICAL FIELD

The present invention relates to a polymer useful as a raw material for cosmetics and the like, a method for producing the polymer, and a composition containing the polymer. The present invention also relates to a method for producing compounds useful as monomers for synthesis of the polymer compound. The present invention further relates to a fluorescence-labeled polymer, and a method for protecting or improving skin.

BACKGROUND ART

Skin conditions greatly influence people's appearance, and skin also plays an important role, i.e., it protects living bodies by its barrier function from pathogenic microorganisms, external physical stimuli such as heat, dryness, moisture and friction, toxic substances and the like. Therefore, it must be said that it is a big object to protect or improve skin from the viewpoints of maintenance of beauty, health, living bodies and the like.

As currently used approaches for treating damaged skin or injured skin, there can be mentioned winding a bandage on such damaged skin to protect it from external stimuli, pathogenic organisms and the like, applying compositions for topical to skin containing anti-inflammatory or anti-bacterial ingredients, or spraying such compositions as aerosol and the like. These approaches are all based on separation of the skin from factors harmful for skin, or prevention of penetration of such factors, and they do not directly act on the skin. Thus, recovery of skin functions itself is left to depend on physiological functions. That is, there have currently been no means for positively recovering the skin structure itself.

Moreover, there frequently exist on skin surface damages degrading proper functions or appearance of skin, even though they are not so serious as those generally referred to as damaged skin, injured skin or rough skin. For such mild skin damages, there have also been only the same procedures as those for damaged skin and injured skin mentioned above.

By the way, since molecular weight of polymers is easily controlled, and polymers of various properties can be prepared by selecting monomers, they are utilized in various fields. Furthermore, in recent years, there have been developed polymers contributing improvements of people's appearance and health in the fields of cosmetics, pharmaceuticals and the like, including those for coiffure agents, moisturizers, biomaterial polymers and the like. However, there have never been known polymers having groups exhibiting affinity for skin on their structures, and thereby exhibiting beneficial effects on skin functions, for example, excellent moisturizing property, skin damage healing property and the like, nor any conception of development of such polymers.

In damaged portions of body surfaces including skin and hair, structures of peptides, collagen, keratin and the like are disordered or destroyed, and there are many free amino groups, free carboxyl groups and the like derived from the aforementioned disorder or destruction. Further, the structures of the aforementioned polymers are characterized by a backbone hydrocarbon and amino acid residues contained in its side chains. Therefore, it is estimated that such amino acid residues in the polymers are attached to the free amino groups, free carboxyl groups etc. by affinity so that the body surface conditions should be brought toward better conditions, and the body surfaces should be protected or improved by the polymers adsorbed on the damaged portions.

On the other hand, while there have been used anti-bacterial agents, protection of damaged portions from external stimuli with bandages and the like as conventional approaches for protection or improvement of body surfaces, they all do not act on the structures of the body surfaces themselves. That is, the aforementioned function for restoring the structures of body surfaces, which is estimated to be possessed by the polymers, has never been used in the conventional approaches. Therefore, in order to investigate this function, it is necessary to quantitatively label the polymers, and to quantitatively determine their behaviors such as presence and distribution.

As a common technique for labeling compounds, introduction of labeled groups into proper sites of molecules can be mentioned. According to this technique, a defined number of labeled groups can be introduced per molecule, and thus quantitative labeling can be realized. However, because polymer molecules do not have a constant degree of polymerization, a defined amount of labeling groups cannot be introduced into each constituent monomer even by the aforementioned labeling technique. That is, there has been no method for quantitatively labeling polymers so far.

DESCRIPTION OF THE INVENTION

An object of the present invention is to provide a polymer that has, in its partial structure, a group exhibiting affinity for skin, and exhibits beneficial effects on skin functions thanks to the skin affinity group.

Another object of the present invention is to provide a composition containing a polymer that has, in its partial structure, a group exhibiting affinity for skin, and exhibits beneficial effects on skin functions thanks to the skin affinity group.

A further object of the present invention is to provide a method for quantitatively labeling a polymer or a salt thereof.

In view of the situation described above, the inventors of the present invention earnestly conducted studies to seek a polymer exhibiting beneficial effects on skin functions. As a result, they found a polymer or a salt thereof comprising a compound represented by Formula (1) or a salt thereof as a constituent monomer, or having a structure represented by Formula (9) as a partial structure exhibited affinity for skin, and beneficial effects on skins such as protection and improvement of skin. Thus, they accomplished the present invention.

That is, the present invention provides:

(1) a compound represented by Formula (1):

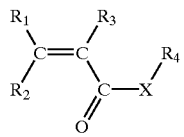

Formula (1)

wherein R1, R2 and R3 each independently represent hydrogen atom, an alkyl group, an alkoxyl group, or an alkylamino group; R4 represents an amino acid residue, a polyamine residue, or an aminoalcohol residue; and X represents oxygen atom or a group represented as NH, or a salt thereof;

(2) the compound according to the above (1), wherein the compound represented by Formula (1) is a compound represented by the following Formula (2);

Formula (2)

wherein R5 represents hydrogen atom or methyl group, R6 represents an amino acid residue, a polyamine residue, or an aminoalcohol residue; and Y represents oxygen atom or a group represented as NH;

(3) the compound according to the above (1) or (2), wherein the compound represented by Formula (1) is a compound represented by any one of Formulae (3) to (8);

Formula (3)

Formula (4)

Formula (5)

Formula (6)

Formula (7)

Formula (8)

(4) a polymer which contains the compound according to any one of the above (1) to (3) as a constituent monomer, or a salt thereof;

(5) a polymer which has a partial structure represented by Formula (9):

Formula (9)

wherein $R_1$, $R_2$ and $R_3$ each independently represent hydrogen atom, an alkyl group, an alkoxyl group, or an alkylamino group; $R_4$ represents an amino acid residue, a polyamine residue, or an aminoalcohol residue; and X represents oxygen atom or a group represented as NH, or a salt thereof;

(6) the polymer according to the above (5), wherein the partial structure represented by Formula (9) is a partial structure represented by Formula (10):

Formula (10)

wherein R5 represents hydrogen atom or methyl group, R6 represents an amino acid residue, a polyamine residue, or an aminoalcohol residue; and Y represents oxygen atom or a group represented as NH;

(7) the polymer according to the above (5) or (6), wherein the partial structure represented by Formula (10) is one or more partial structures selected from partial structures represented by any one of Formulae (11) to (17);

Formula (11)

-continued

Formula (12)
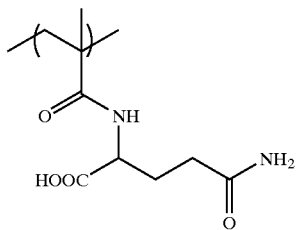

Formula (13)
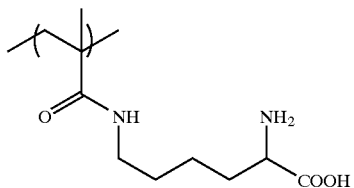

Formula (14)
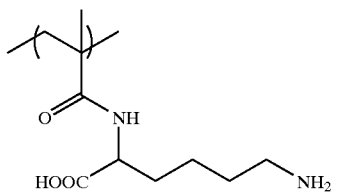

Formula (15)
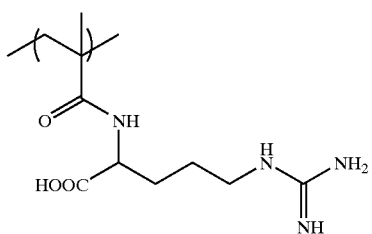

Formula (16)
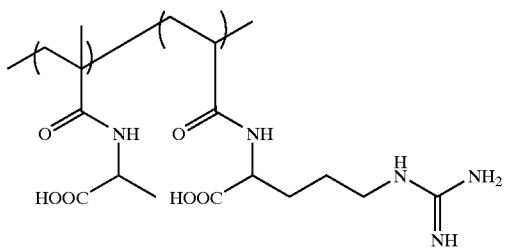

Formula (17)
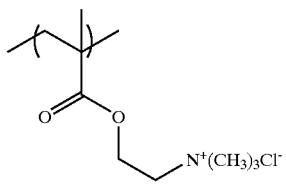

(8) the polymer according to any one of the above (4) to (7), wherein molecular weight of the polymer is 5000–1,000,000;

(9) a method for producing of the polymer according to any one of the above (4) to (8), wherein a compound represented by Formula (1) or a salt thereof is polymerized as a raw material monomer;

(10) a composition which contains the polymer according to the above (4) and/or a salt thereof;

(11) a composition containing the polymer according to any one of the above (5) to (8) or a salt thereof;

(12) the composition according to the above (10) or (11), wherein the polymer and/or a salt thereof is a polymer or a salt thereof produced by polymerized only a compound represented by Formula (1) or a salt thereof;

(13) the composition according to any one of the above (10) to (12), which is composition for topical to skin;

(14) the composition according to any one of the above (10) to (12), which is a cosmetic;

(15) a method for producing a compound represented by Formula (18):

Formula (18)
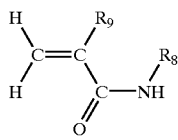

wherein R8 represents lysine, arginine, ornithine, or citrulline residue, and R9 represents methyl group or hydrogen atom, or a salt thereof, which method comprises steps of performing condensation reaction of one or more compounds selected from lysine, arginine, ornithine, citrullines, and salts thereof; and one or more compounds selected from methacrylic acid, acrylic acid, and acid halides thereof, making the reaction mixture acidic, subjecting the mixture to liquid-liquid extraction with an organic solvent and water, and neutralizing the aqueous layer;

(16) the method according to the above (15), which comprises a step of lowering water content with an organic solvent capable of azeotroping with water;

(17) the method according to the above (16), wherein the organic solvent capable of azeotroping with water is n-propanol, isopropanol, or n-butanol;

(18) a method for protecting or improving skin, which comprises a step of treating free amino groups and/or free carboxyl groups on the skin with a group exhibiting affinity for the amino groups and/or a group exhibiting affinity for the carboxyl groups;

(19) the method for protecting or improving skin according to the above (18), wherein the group exhibiting affinity for the free amino groups on the skin is carboxyl group, and/or the group exhibiting affinity for the free carboxyl groups on the skin is one or more kinds of groups selected from amino group, ammonium group, and guanidyl group;

(20) the method for protecting or improving skin according to the above (18) or (19), wherein the free amino groups and/or the free carboxyl groups on the skin are treated with a substance having two kinds of groups, a group exhibiting affinity for the amino groups and a group exhibiting affinity for the carboxyl groups, in a single molecule;

(21) the method for protecting or improving skin according to any one of the above (18) to (20), wherein a source or sources of the group exhibiting affinity for the free amino groups on the skin and/or the group exhibiting affinity for the free carboxyl groups on the skin is(are) an amino acid moiety of an amino acid pendant type polymer and/or an aminoalcohol moiety of an aminoalcohol pendant type polymer;

(22) the method for protecting or improving skin according to any one of the above (18) to (21), wherein backbone of the amino acid pendant type polymer and/or the aminoalcohol pendant type polymer has a structure of a homopolymer or copolymer of acrylic acid and/or methacrylic acid;

(23) the method for protecting or improving skin according to any one of the above (18) to (22), wherein the amino acid pendant type polymer and/or the aminoalcohol pendant type polymer has a molecular weight of 5000–1,000,000;

(24) the method for protecting or improving skin according to any one of the above (18) to (23), wherein the amino acid pendant type polymer and/or the aminoalcohol pendant type comprises a polymerization monomer represented by the following Formula (19):

Formula (19)
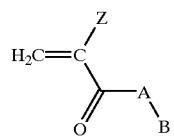

wherein Z represents hydrogen atom or methyl group, A-B represents an amino acid or an aminoalcohol, and A represents oxygen atom or NH;

(25) the method for protecting or improving skin according to any one of the above (18) to (24), wherein the polymerization monomer is one or more compounds selected from the group consisting of compounds represented by any one of the following Formulae (3) to (8):

Formula (3)
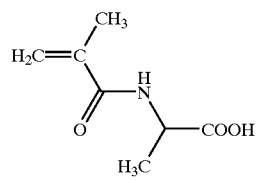

Formula (4)
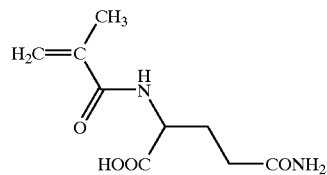

Formula (5)
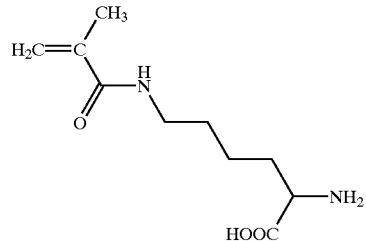

Formula (6)
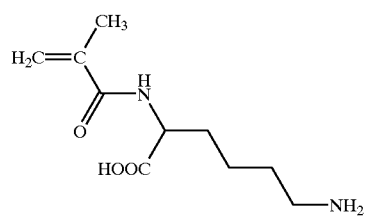

Formula (7)
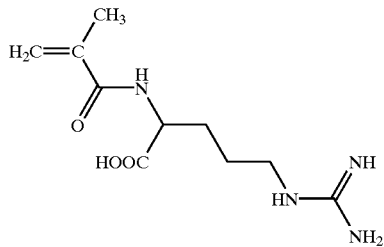

Formula (8)
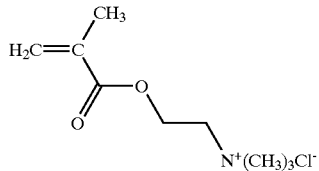

(26) a compound represented by Formula (21):

Formula (21)
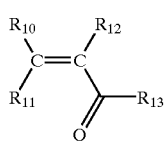

wherein $R_{10}$ to $R_{12}$ each independently represent hydrogen atom or an alkyl group having 1–4 carbon atoms, and $R_{13}$ represents a group comprising a labeled group, or a salt thereof;

(27) the compound according to the above (26), wherein $R_{13}$ in Formula (21) is a group represented as $-NH-(CH_2)_n-R_{14}$ where n is an integer of 2–10, and $R_{14}$ represents a labeled group;

(28) the compound according to the above (26), wherein the labeled group is dansyl group;

(29) the compound according to the above (26), wherein the compound represented by Formula (21) is a compound represented by Formula (22):

Formula (22)
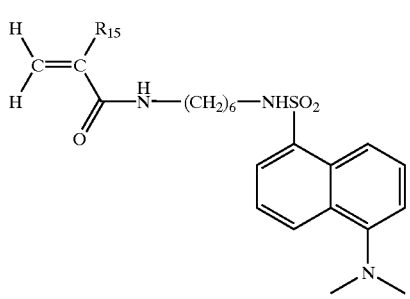

wherein $R_{15}$ represents hydrogen atom or methyl group;

(30) a polymer which contains, together with one or more compounds selected from the group consisting of the compounds according to any one of the above (26) to (29), one or more compounds represented by Formula (23):

Formula (23)

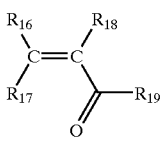

wherein R16 to R18 each independently represent hydrogen atom or an alkyl group having 1–4 carbon atoms, and R19 represents an amino acid residue or salts thereof, as constituent monomers, or a salt thereof;

(31) the polymer according to the above (30), wherein the compound represented by Formula (23) is one or more compounds selected from compounds represented by any one of Formulae (3) to (8):

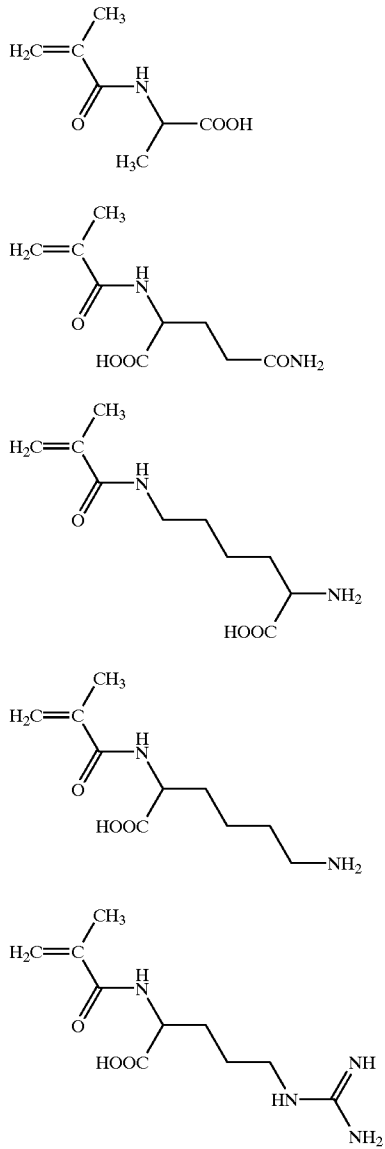

Formula (3)

Formula (4)

Formula (5)

Formula (6)

Formula (7)

-continued

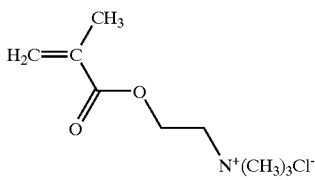

Formula (8)

(32) a method for identifying a group exhibiting affinity for amino acid residues by utilizing the polymer according to the above (30) or (31); and

(33) a method for differentiating skin by utilizing the identification method according to the above (32).

Hereafter, the present invention will be explained in detail.

<1> Compound Represented by Formula (1) or Salt Thereof

The compound represented by Formula (1) or a salt thereof of the present invention will be explained. Polymers or salts thereof containing the compound represented by Formula (1) or a salt thereof exhibit beneficial effects on skin functions. That is, the compound represented by a Formula (1) or a salt thereof can be used as the monomer, i.e., a raw material of the polymers that exhibit the advantages of the present invention.

In Formula (1), R1, R2 and R3 each independently represent hydrogen atom, an alkyl group, an alkoxyl group, or an alkylamino group. The alkyl group used herein is not particularly limited, but it is preferably a linear, branched or cyclic alkyl group having 1–4 carbon atoms. Examples of the alkyl group include, for example, methyl group, ethyl group, n-propyl group, n-butyl group, i-propyl group, i-butyl group, sec-butyl group, tert-butyl group, cyclopropyl group, cyclobutyl group and the like.

The alkoxyl group is also not particularly limited, but it is preferably a linear, branched or cyclic alkoxyl group having 1–4 carbon atoms. Examples of the alkoxyl group include, for example, methoxyl group, ethoxyl group, n-propoxyl group, n-butoxyl group, i-propoxyl group, i-butoxyl group, sec-butoxyl group, tert-butoxyl group, cyclopropoxyl group, cyclobutoxyl group and the like.

The alkylamino group herein used is also not particularly limited, but it is preferably an alkylamino group having an alkyl portion consisting of a linear, branched or cyclic alkyl group having 1–4 carbon atoms. It may have 1–3 alkyl groups. However, when it has three alkyl groups, it is preferably form a quaternary salt group with an acid. Examples of such the alkyl group include, for example, methyl group, ethyl group, n-propyl group, n-butyl group, i-propyl group, i-butyl group, sec-butyl group, tert-butyl group, cyclopropyl group, cyclobutyl group and the like. Specific examples of the alkylamino group include, for example, methylamino group, ethylamino group, n-propylamino group, n-butylamino group, i-propylamino group, i-butylamino group, sec-butylamino group, tert-butylamino group, cyclopropylamino group, cyclobutylamino group, dimethylamino group, diethylamino group, di-n-propylamino group, di-n-butylamino group, di-i-propyl amino group, di-i-butylamino group, di-sec-butylamino group, di-tert-butylamino group, dicyclopropylamino group, dicyclobutylamino group, trimethylammonium group, triethylammonium group and the like.

It is preferred that R1, R2 and R3 each independently represent hydrogen atom or methyl group among the above-mentioned groups. Further, as for the combination of R1, R2 and R3, the combination [R1, R2, R3] is particularly preferably [hydrogen atom, hydrogen atom and hydrogen atom] or [hydrogen atom, hydrogen atom and methyl group]. This is because raw materials for compounds having such combinations are marketed, and they can readily be obtained.

In Formula (1), R4 represents an amino acid residue, a polyamine residue, or an aminoalcohol residue. The amino acid residue is not particularly limited so long as it is derived from usual known amino acids. Specific examples of such amino acid include glycine, alanine, glutamine, lysine, arginine and the like. Among these, lysine residue is particularly preferred. This is because the polymer or a salt thereof containing lysine residues as a constituent monomer exhibits particularly excellent effect for skin protection or improvement.

In the polyamine residue, the polyamine used herein is an amine having, in one molecule, two or more amino groups which may be substituted with an alkyl group. Specific examples of the polyamine include, for example, diamines, triamines, tetraamines, those compounds consisting the foregoing amines whose amino group is substituted with an alkyl group, and the like. Among these polyamines, diamines and diamines whose amino group is substituted with an alkyl group are more preferred, since such compounds provides good feeling upon use. Particularly preferred diamines are ethylenediamine, 1,4-diamino-n-butane, 1,6-diamino-n-hexane and the like, because of availability of raw materials therefor.

In the aminoalcohol residue, the aminoalcohol used herein means an organic compound which has, in a single molecule, an amino group which may be substituted with an alkyl group and an alcholic hydroxyl group. The aminoalcohol is not particularly limited so long as it is a usual known aminoalcohol, and specific examples thereof include ethanolamine, trimethylaminoethanol and the like.

In Formula (1), X represents oxygen atom or a group represented as NH.

The salt of the compound represented by Formula (1) is not particularly limited. Specifically, there can be mentioned mineral acid salts such as salts of hydrochloric acid, sulfuric acid, nitric acid and phosphoric acid, organic acid salts such as salts of citric acid, oxalic acid, fumaric acid, maleic acid, formic acid, acetic acid, methanesulfonic acid, benzenesulfonic acid and p-toluenesulfonic acid, carbonic acid salts, alkali metal salts such as salts of sodium and potassium, alkaline earth metal salts such as salts of calcium and magnesium, and the like.

Among the compounds represented by Formula (1) and salts thereof, those compounds represented by Formulae (3) to (8) and salts thereof are preferred, since those polymers and salts thereof containing them as constituent monomers show particularly excellent protection or improvement of skin.

The compound represented by Formula (1) or a salt thereof can be produced based on the following Reaction Scheme (1). That is, the compound represented by Formula (1) or a salt thereof can be obtained by ester condensation or amide condensation of a compound represented by Formula (a) or a salt thereof and a compound represented by Formula (b) or a salt thereof.

Reaction Scheme (1)

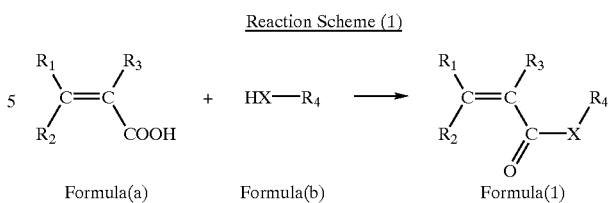

Formula(a)　　Formula(b)　　Formula(1)

In the formula, R1, R2 and R3 each independently represent hydrogen atom, an alkyl group, an alkoxyl group, or an alkylamino group; R4 represents an amino acid residue, a polyamine residue, or an aminoalcohol residue; and X represents oxygen atom or a group represented as NH.

A salt of the compound represented by Formula (1) may be formed during the aforementioned reaction, or after the compound represented by Formula (1) is once isolated. The salt formation can be carried out in a conventional manner. For example, a salt can be produced by mixing a compound represented by Formula (1) and an acid or base in an appropriate ratio in an organic or inorganic solvent.

Because polymers and salts thereof containing the compound represented by Formula (1) or a salt thereof as constituent monomers exhibit beneficial effects on skin functions as will be described in examples mentioned below, and are suitable as a raw material of cosmetics, the compound represented by Formula (1) can also be said to be very useful as the raw material therefor.

<2> Polymer of the Present Invention

The polymer or a salt thereof of the present invention which contains the compound represented by Formula (1) or a salt thereof as constituent monomers will be explained. The polymer may be a homopolymer, graft copolymer, block copolymer or random copolymer that contains one or more sorts of the compound represented by Formula (1) or a salt thereof, and if desired, other monomers usually used for polymers such as acrylic acid and esters thereof, methacrylic acid and esters thereof, vinyl alcohol and the like as constituent monomers. The polymer exhibits beneficial effects on skin functions such as moisturizing effect and skin protection effect as will be demonstrated in examples mentioned below.

The polymer should be a polymer or a salt thereof which comprises a compound represented by Formula (1) or a salt thereof as constituent monomers, and the constituent monomers may consist only of the compound represented by Formula (1) or a salt thereof, or may also contain compounds other than the compound represented by Formula (1) or a salt thereof as constituent monomers to such an extent that the advantages of the present invention should not be degraded. Such monomers used as comonomers are not particularly limited so long as they are constituent monomers used in polymers generally used for cosmetics, compositions for topical to skin and the like. Specific examples thereof include, for example, ethylene, vinyl alcohol and the like. When other compounds are used as constituent monomers, the polymer sequence may be, for example, a graft copolymer, block copolymer, or random copolymer.

While the ratio of the compound represented by Formula (1) or a salt thereof relative to the whole constituent monomers may vary depending on the kinds of monomers used together and the like, the ratio is preferably 10% by weight or more, more preferably 50% by weight or more, and it is particularly preferred that the polymer comprises only the monomer of the present invention as constituent monomers. This is because the beneficial effects on skin functions of the polymer of the present invention decreases as the ratio of the monomer of the present invention decreases. The polymer can be obtained by performing solution polymerization or emulsion polymerization of these constituent monomers in the presence of a polymerization initiator. The polymer obtained as described above has a partial structure represented by Formula (9).

The kind of the salt is not particularly limited so long as it is a physiologically acceptable salt. Specific examples thereof include, for example, mineral acid salts such as salts of hydrochloric acid, sulfuric acid, nitric acid and phosphoric acid, organic acid salts such as salts of citric acid, oxalic acid, fumaric acid, maleic acid, formic acid, acetic acid, methanesulfonic acid, benzenesulfonic acid and p-toluenesulfonic acid, carbonic acid salts, alkali metal salts such as salts of sodium and potassium, alkaline earth metal salts such as salts of calcium and magnesium, and the like.

The polymer of the present invention or a salt thereof can be produced in a conventional manner. A salt can be obtained by using salts as the monomers, and a salt may be produced after polymerization.

Therefore, R1 to R4 and X in Formula (9) correspond to R1 to R4 and X in Formula (1), respectively. That is, R1 to R4 and X in Formula (9) have the same meanings as R1 to R4 and X in Formula (1), respectively.

In Formula (9), R1, R2 and R3 each independently represent hydrogen atom, an alkyl group, an alkoxyl group or an alkylamino group. The alkyl group used herein is not particularly limited, but it is preferably a linear, branched or cyclic alkyl group having 1–4 carbon atoms. Examples of the alkyl group include, for example, methyl group, ethyl group, n-propyl group, n-butyl group, i-propyl group, i-butyl group, sec-butyl group, tert-butyl group, cyclopropyl group, cyclobutyl group and the like.

The alkoxyl group is also not particularly limited, but it is preferably a linear, branched or cyclic alkoxyl group having 1–4 carbon atoms. Examples of the alkoxyl group include, for example, methoxyl group, ethoxyl group, n-propoxyl group, n-butoxyl group, i-propoxyl group, i-butoxyl group, sec-butoxyl group, tert-butoxyl group, cyclopropoxyl group, cyclobutoxyl group and the like.

The alkylamino group herein used is also not particularly limited, but it is preferably an alkylamino group having an alkyl portion consisting of a linear, branched or cyclic alkyl group having 1–4 carbon atoms. It may have 1–3 alkyl groups. However, when it has three alkyl groups, it is preferably form a quaternary salt group with an acid. Examples of such the alkyl group include, for example, methyl group, ethyl group, n-propyl group, n-butyl group, i-propyl group, i-butyl group, sec-butyl group, tert-butyl group, cyclopropyl group, cyclobutyl group and the like. Specific examples of the alkyl amino group include, for example, methylamino group, ethylamino group, n-propylamino group, n-butylamino group, i-propylamino group, i-butylamino group, sec-butylamino group, tert-butylamino group, cyclopropylamino group, cyclobutylamino group, dimethylamino group, diethylamino group, di-n-propylamino group, di-n-butylamino group, di-i-propylamino group, di-i-butylamino group, di-sec-butylamino group, di-tert-butylamino group, dicyclopropylamino group, dicyclobutylamino group, trimethylammonium group, triethyl ammonium group and the like.

It is preferred that R1, R2 and R3 each independently represent hydrogen atom or methyl group among the above-mentioned groups. Further, as for the combination of R1, R2 and R3, the combination [R1, R2, R3] is preferably [hydrogen atom, hydrogen atom and hydrogen atom] or [hydrogen atom, hydrogen atom and methyl group]. This is because raw materials for compounds having such combinations are marketed, and they can readily be obtained.

In Formula (9), R4 represents an amino acid residue, a polyamine residue or an aminoalcohol residue. The amino acid residue is not particularly limited so long as it is derived from usual known amino acids. Specific examples of such amino acid include glycine, alanine, glutamine, lysine, arginine and the like. Among these, lysine residue is particularly preferred, because the polymer or a salt thereof containing lysine residues as a constituent monomer exhibits particularly excellent effect for skin protection or improvement.

In the polyamine residue, the polyamine used herein is an amine having, in one molecule, two or more amino groups which may be substituted with an alkyl group. Specific examples of the polyamine include, for example, diamines, triamines, tetraamines, those compounds consisting the foregoing amines whose amino group is substituted with an alkyl group, and the like. Among these polyamines, diamines and diamines whose amino group is substituted with an alkyl group are more preferred, since such compounds provides good feeling upon use. Particularly preferred diamines are ethylenediamine, 1,4-diamino-n-butane, 1,6-diamino-n-hexane and the like, because of availability of raw materials for the production thereof.

In the aminoalcohol residue, the aminoalcohol used herein is an organic compound which has, in a single molecule, an amino group which may be substituted with an alkyl group and an alcholic hydroxyl group. The aminoalcohol is not particularly limited so long as it is a usual known aminoalcohol, and specific examples thereof include ethanolamine, trimethylaminoethanol and the like.

In Formula (9), X represents oxygen atom or a group represented as NH.

The salt of the polymer comprising a partial structure represented by Formula (9) is not particularly limited. specifically, there can be mentioned mineral acid salts such as salts of hydrochloric acid, sulfuric acid, nitric acid and phosphoric acid, organic acid salts such as salts of citric acid, oxalic acid, fumaric acid, maleic acid, formic acid, acetic acid, methanesulfonic acid, benzenesulfonic acid and p-toluenesulfonic acid, carbonic acid salts, alkali metal salts such as salts of sodium and potassium, alkaline earth metal salts such as salts of calcium and magnesium, and the like.

Among the partial structures represented by Formula (9), those partial structures represented by any one of Formulae (11) to (17) are preferred, since those polymers and salts thereof containing those partical structures show particularly excellent protection or improvement of skin.

The polymer of the present invention has a molecular weight of, preferably 5000–1,000,000, more preferably 10,000–100,000, because polymers or salts thereof with a molecular weight in such a range show particularly excellent feeling upon use, and excellent effects on the skin functions. Because the polymer of the present invention has a structure of which has the above groups having affinity for skin are suspended from a polymer backbone, the polymer of the present invention will be referred to as an amino acid (aminoalcohol) pendant type polymer.

When the amino acid (aminoalcohol) pendant type polymer of the present invention is used, only the amino acid (aminoalcohol) pendant type polymer of the present invention may be used. However, it may be used with one or more other ingredients as a composition so long as the advantages of the present invention are not degraded. As such the composition, compositions for topical to skin including cosmetics, pharmaceutical for topical to skin, disinfectants and the like are preferred, and cosmetics are particularly preferred among these. The form of the composition is not particularly limited so long as it is one usually used for composition for topical to skin. For example, the form of the composition may be an ointment based on vaseline and water-absorbing ointment, cream, emulsion, lotion, gel, solution or the like.

<3> Method for Producing the Compound

Among the compounds represented by Formula (1), those compounds represented by Formula (18) (compounds of Formula (1) having hydrogen atoms as R1 and R2, methyl group or hydrogen atom as R3, NH as X, and lysine, arginine, ornithine, or citrulline residue as R4) can be produced by carrying out condensation reaction of one or more kinds of compounds selected from lysine, arginine, ornithine, citrullines, and salts thereof; and one or more kinds of compounds selected from methacrylic acid, acrylic acid, and acid halides thereof, making the reaction mixture acidic, subjecting the mixture to liquid-liquid extraction with an organic solvent and water, and neutralizing the aqueous layer.

The compound represented by Formula (18) can be produced by condensation of, for example, an amino acid and methacrylic acid. However, because a diamide compound, for example, is produced during the condensation reaction, it is difficult to separate a target compound from such a by-product and remaining raw materials. Therefore, means for reducing such impurities has been desired in order to control functions of functional polymers.

Adjustment of pH and purification by liquid-liquid extraction are usual means for post-treatment of chemical reactions. However, because the compounds represented by Formula (18) are novel, and hence their physicochemical properties have not been known, it has been impossible to expect that, in the synthesis of the compounds represented by Formula (18), their purity could be markedly improved by transferring the compounds into an aqueous layer under an acidic condition, washing the layer with an organic solvent, neutralizing it, extracting it with an alcohol, and subjecting it to desalting and desolvation. However, the inventors of the present invention found that the compounds represented by Formula (18) or salts can be obtained with high purity by the steps of making the reaction mixture acidic after the condensation reaction, subjecting it to liquid-liquid extraction with an organic solvent and water, and neutralizing the aqueous layer.

Examples of the amino acid that can be used for the production method of the present invention are one or more kinds of amino acids selected from lysine, arginine, ornithine, and citrulline. Among these, lysine is most preferred, because the functional polymers obtained by using lysine exhibit excellent feeling upon use. While these amino acids can be used in their free form, it is more preferable to use their salts. Among their salts, salts of hydrochloride are particularly preferred, because these amino acids are often marketed as salts, in particular, many kinds of salts of hydrochloride are marketed and are readily obtained.

As one or more kinds of compounds selected from methacrylic acid, acrylic acid, and acid halides thereof, the acid halides are preferred because they exhibit good reactivity with the aforementioned amino acids, and realize the condensation reaction in a suitable manner. As the acid halide compounds, either commercially available compounds or those produced by halogenation of methacrylic acid or acrylic acid with a halogenating agent such as thionyl chloride. Examples of the acid halide include acid chlorides, acid bromides, acid iodides and the like. Among these, acid chlorides are preferred, because their production is easy. Among methacrylic acid, acrylic acid, and acid halides thereof, methacryl acid chloride is particularly preferred, because of its good reactivity mentioned above and availability as well as excellent feeling upon use of functional polymers produced by polymerizing monomers obtained from that compound. When methacrylic acid or acrylic acid is used, a halogenating agent such as thionyl chloride, or other suitable condensing agents such as chloroformic acid esters may be used.

The condensation reaction of one or more kinds of compounds selected from lysine, arginine, ornithine, citrullines, and salts thereof; and one or more kinds of compounds selected from methacrylic acid, acrylic acid, and acid halides thereof may be usual acylation reaction of amino group, and performed in a conventional manner. As for the molar ratio of the raw materials, the ratio of one or more kinds of compounds selected from methacrylic acid, acrylic acid, and acid halides thereof to one or more kinds of compounds selected from lysine, arginine, ornithine, citrullines, and salts thereof may be usually 10:1-1:2, preferably 5:1-1:2, more preferably 3:1-1:2. With such a range, the compound represented by Formula (18) can be obtained with an excellent yield or excellent final purity. When methacrylic acid or acrylic acid is used, the condensing agent is not particularly limited, and a usually used one may be used. For example, halogenating agents such as thionyl chloride as well as chloroformic acid esters may be used.

In a specific example of the condensation reaction of one or more kinds of compounds selected from lysine, arginine, ornithine, citrullines, and salts thereof; and one or more kinds of compounds selected from methacrylic acid, acrylic acid, and acid halides there of, for example, one or more kinds of compounds selected from lysine, arginine, ornithine, citrullines, and salts thereof are added to water, and the reaction mixture is adjusted to neutral or weakly acidic condition, and added dropwise with methacryl acid chloride or acrylic acid chloride with stirring and ice cooling. If necessary, a base may be added to the reaction mixture to maintain it neutral or weakly acidic, and the reaction mixture may be stirred at an ordinary temperature for 1 minute to 24 hours after the methacryl acid chloride or acrylic acid chloride was added dropwise.

In the production method of the present invention, impurities are transferred into an organic layer by concentrating the reactants as required after the condensation reaction, and subjecting them to liquid-liquid extraction with an organic solvent immiscible with water and water under an acidic condition. In this step, it is important to perform the extraction so that the impurities should migrate into the organic layer, and the compound represented by the Formula (18) should not migrate into the aqueous layer.

When the reaction mixture is made acidic, it preferably has pH of 0–3. In this range, impurities can be eliminated efficiently. While the acid to be used is not particularly limited, hydrochloric acid is preferred because it makes it easy to eliminate salt produced during the subsequent neutralization.

The organic solvent used for performing the liquid-liquid extraction with an organic solvent and water is not particularly limited so long as it is immiscible with water at any ratio and can realize the liquid-liquid extraction with water. Specific examples thereof include, for example, ethyl acetate, benzene, chloroform, dichloromethane and the like. These solvents give a high final purity of the compound represented by Formula (18). The liquid-liquid extraction may be performed in a conventional manner. As for the amount of the solvent, water and the organic solvent may be preferably used in an amount of 10 to 1000 times as much as the expected amount of the compound represented by the Formula (18). The liquid-liquid extraction may be performed once or more times until sufficient separation and purification of the compound represented by Formula (18) or a salt thereof can be attained.

In a more preferred embodiment of the production method of the present invention, the aqueous layer purified by the aforementioned liquid-liquid extraction is neutralized. The neutralization is preferably performed to pH 6.0–8.0, more preferably pH 6.5–7.5, particularly preferably pH 7.0. Such a pH range serves to increase the purity of the compound represented by Formula (18). The base used for the neutralization may be a hydroxide, hydrogencarbonate or carbonate of alkali metals and alkaline earth metals, and sodium hydroxide is particularly preferred since elimination of the salt generated by the neutralization is easy. In the production method of the present invention, it is preferable to add a polymerization inhibitor such as p-methoxyphenol before or after the neutralization step.

The aqueous solution obtained as described above is a composition containing a salt generated by the neutralization and the compound represented by Formula (18), and it may be concentrated if needed. By extracting the compound represented by Formula (18) from this composition, the compound represented by Formula (18) will be obtained with high purity. In this case, it is preferable to use a solvent which can azeotrope with water as the solvent to be used, not only because use of such a solvent can eliminate impurities, but also because the use of such a solvent reduces water content of the solution containing the compound represented by Formula (18) during the concentration process to realize crystallization of the compound. Since the compound represented by Formula (18) is excellent in moisture retention property, it is difficult to be crystallized it without this step. Of course, these impurities may also be eliminated by ion exchange or chromatography techniques, and use of such purification techniques also fall within the scope of the present invention. However, use of the above solvent which can azeotrope with water is preferred to the above purification techniques, because of its simplicity and low cost.

The organic solvent which can azeotrope with water is not particularly limited. Preferred examples thereof include, for example, fatty alcohols having 2–4 carbon atoms, and more specifically, ethanol, n-propanol, i-propanol, n-butanol, i-butanol, sec-butanol, tert-butanol and the like can be mentioned. Among these, n-propanol, i-propanol, and n-butanol are more preferred, and i-propanol and n-butanol are particularly preferred, since they makes it easier to eliminate impurities, crystallize the compound represented by Formula (18), and hence they give higher purity and the like. The organic solvent which can azeotrope with water used herein may consist of one kind of such a solvent or a combination of two or more kinds of such solvents as required.

Thus, the compound represented by the Formula (18) obtained by the production method of the present invention is obtained with high purity, and therefore the polymer obtained from the compound as a raw material will have excellent quality.

<4> Composition of the Present Invention

The composition of the present invention is characterized by comprising a polymer containing the compound represented by Formula (1) and/or a salt thereof as constituent monomers as an essential component. Preferred examples of the compound represented by Formula (1) are the compounds represented by any one of Formula (3) to (8).

As the composition, cosmetics, pharmaceuticals for topical to skin, disinfectants and the like are preferred, and cosmetics are particularly preferred, because the polymers of the present invention are adsorbed by skin with excellent affinity and serve as an excellent protective membrane, and thus the composition of the present invention exhibits its effects more efficiently on the skin with higher safety. In cosmetics, the essential ingredient itself functions as a protection membrane, and enhances the effects of other ingredients. The composition of the present invention may contain one kind of the polymer containing the compound represented by Formula (1) as constituent monomers or a salt thereof, or contain two or more kinds of the polymer or a salt thereof in combination. A preferred content of the compound in total ranges 0.001–20% by weight, more preferably 0.01–10% by weight. The composition of the present invention may contain, in addition to the essential ingredient, i.e., the polymer containing the compound represented by Formula (1) as constituent monomers and/or a salt thereof, other arbitrary ingredients used for similar compositions for topical to skin to such an extent that does not degrade the advantages of the present invention. Examples of such arbitrary ingredients include, for example, hydrocarbons such as vaseline and microcrystalline waxes, esters such as jojoba oil and sperm whale, triglycerides such as beef tallow and olive oil, higher alcohols such as cetanol and oleyl alcohol, fatty acids such as stearic acid and oleic acid, polyhydric alcohols such as glycerin and 1,3-butanediol, nonionic surface active agents, anionic surface active agents, cationic surface active agents, amphoteric surface active agents, ethanol, thickeners such as Carbopole, antiseptics, ultraviolet absorbers, antioxidants, coloring matters, fine particles and the like. The composition of the present invention is produced by formulating these ingredients in a conventional manner.

<5> Method for Protecting or Improving Skin According to the Present Invention

The method for protecting or improving skin according to the present invention is performed by treating free amino groups and/or free carboxyl groups on the skin with a group exhibiting affinity for the amino groups and/or a group exhibiting affinity for the carboxyl groups.

The skin which can be treated with the method of the present invention is not particularly limited, and the term "skin" has the generic meaning usually implied by the term. However, it collectively means, inter alia, skins which suffer certain skin dysfunctions, for example, those exhibiting reduced moisture retention function, and therefore exhibiting crust and the like, those unable to prevent penetration of irritants due to reduced barrier function and the like. Such skins include not only those having troubles such as usual rough skin, but also those exhibiting slighter conditions, and are characterized by a disordered structure of proteins of the surface portion of the skins, and presence of free amino groups and free carboxyl groups. The free amino groups and the free carboxyl groups referred to in the present invention are derived from the disordered structure of proteins of the surface portions of skin.

SDS-damaged skin model and ultraviolet ray-damaged skin model will be explained hereinafter, which are frequently used for explaining the relationship between damages of skin and amino groups and carboxyl groups on the skin in the field of cosmetics and the like.

<SDS-damaged Skin Model>

This damaged skin model prepared by using sodium dodecylsulfate (abbreviated as "SDS" hereinafter) is a model of rough skin caused by a chemical irritant such as surface active agent. This model was prepared as follows. That is, the model was prepared by applying 5% SDS aqueous solution to back skin (50 mm×30 mm) of hairless mice (male, body weight: 25–30 g) twice a day in an amount of 0.1 ml for each application for three days. Infrared absorption spectrum of skin horny layer of the skin was measured. Judging from differences of the spectrum at 1625–1685 cm$^{-1}$ and 1510–1565 cm$^{-1}$, the skin of the damaged skin model had increased carboxyl groups compared with non-treated skin, and thus increase of free carboxyl groups on the skin was confirmed. Moreover, structural change of keratin was also observed, and therefore disordered structure on the skin, which meant damage, was surely confirmed.

<Ultraviolet Ray-damaged Model>

A damaged skin model was prepared by irradiating back skin (50 mm×30 mm) of hairless mice (male, body weight: 25–30 g) once with an ultraviolet ray of 3 MED. Infrared absorption spectrum of skin horny layer of the skin was measured. Like the SDS-damaged skin, the skin of this damaged skin model also had increased carboxyl groups compared with non-treated skin, and thus increase of free carboxyl groups on the skin was confirmed. Moreover, structural change of keratin was also observed, and therefore disordered structure on the skin, which meant damage, was surely confirmed.

The inventors of the present invention earnestly studied in order to realize protection of skin functions, and found that free amino groups and/or free carboxyl groups on the skin might be restored to the condition before the formation of them, i.e., the condition where the skin exhibited proper functions, by treating the groups with a group exhibiting affinity for the amino groups and/or the carboxyl groups, and thereby the skin functions could be protected and improved.

The group exhibiting affinity for free amino groups on skin may be a group that is known to exhibit chemical affinity for amino groups. Preferred examples thereof include, for example, acidic groups such as carboxyl group, sulfonyl group and phosphoric acid group, halogen groups, phenoxy group and the like, and particularly preferred is carboxyl group. The acidic groups such as carboxyl group, sulfonyl group and phosphoric acid group may form salts so long as the advantages of the present invention should not be degraded.

The group exhibiting affinity for free carboxyl groups on skin may be a group that is known to exhibit chemical affinity for carboxyl groups. Preferred examples thereof include, for example, amino group, secondary amino groups such as methylamino group and ethylamino group, tertiary amino groups such as ammonium group, guanidyl group and the like. Among these, amino group and ammonium group are particularly preferred. The basic groups such as amino group and ammonium group may form salts so long as the advantages of the present invention should not be degraded.

In the method for protecting or improving skin of the present invention, the treatment of free amino groups and/or free carboxyl groups on skin is preferably performed by application of a substance having both of the group exhibiting affinity for amino groups and the group exhibiting affinity for carboxyl groups in a single molecule. Such a substance having both of the group exhibiting affinity for free amino groups and the group exhibiting affinity for free carboxyl groups in a single molecule provides attraction by chemical affinity bonding for free amino groups and carboxyl groups on skin at multiple points, and the attracted portions enhance the affinity one another, which leads to more enhanced advantages of the present invention.

In the method for protecting or improving skin of the present invention, a source of the group exhibiting affinity for free amino groups and the group exhibiting affinity for free carboxyl groups is preferably an amino acid moiety of the amino acid pendant type polymer or an aminoalcohol moiety of the aminoalcohol pendant type polymer. The amino acid pendant type polymer used herein is a polymer having a pendant-like structure where an amino acid side chain is suspended from a backbone, and it may be represented as shown in FIG. 1. The aminoalcohol pendant type polymer used herein is a polymer having a pendant-like structure where an aminoalcohol side chain is suspended from a backbone. The amino group of the aminoalcohol side chain may be a primary amino group, secondary amino group, tertiary amino group, or quaternary amino group. As specific examples of the amino acid pendant type polymer and the aminoalcohol pendant type polymer, there can be exemplified, for example, polymers having any one of the partial structures represented by Formula (11) to Formula (17). The side chains of the amino acid pendant type polymer or the aminoalcohol pendant type polymer may form salts, unless such salt formation causes troubles in practical use of the compounds. If such an amino acid pendant type polymer or an aminoalcohol pendant type polymer is used, it becomes easy to adjust the amount, ratio, kind and the like of the group having affinity for free amino groups, or the group having affinity for free carboxyl groups, and therefore it becomes easy to protect or improve skin with various conditions. The polymers can also improve the moisture retention function by normalizing horny layer. Furthermore, the amino acid pendant type polymer exhibits good affinity for living bodies, and therefore it is also particularly excellent in safety.

The amino acid pendant type polymer and the aminoalcohol pendant type polymer used herein also have a function for protecting skin from irritants, dryness, friction and the like by being selectively attracted by affinity to a portion which does not exhibit proper skin functions to form a functional membrane.

The amino acid of the amino acid pendant type polymer used herein is not particularly limited, and usual known amino acids may be used. Preferred examples thereof are alanine, glutamine, lysine, arginine and the like.

The backbone of the amino acid pendant type polymer and/or the aminoalcohol pendant type polymer may have, for example, a structure of homopolymer, graft copolymer, block copolymer, or random copolymer, which are constituted of one or more kinds of monomers selected from acrylic acid, methacrylic acid, vinyl alcohol, vinylbenzene and the like. In particular, those having a structure of homopolymer, graft copolymer, block copolymer or random copolymer of acrylic acid and/or methacrylic acid are preferred, since such polymers are common as raw materials of cosmetics and highly safe.

In the method for protecting or improving skin of the present invention, the amino acid pendant type polymer and the aminoalcohol pendant type polymer preferably have a molecular weight of 5000–1,000,000, more preferably 10,000–100,000. The polymers with a molecular weight in such a range afford good feeling upon practical use of the composition.

Preferred examples of polymerization monomers for the amino acid pendant type polymer and/or the an aminoalcohol pendant type polymer used for the method for protecting or improving skin of the present invention are, for example, those compounds represented by Formula (19). Among those, one or more selected from compounds represented by any one of Formula (3) to Formula (8) can be particularly preferably used, because of availability of raw materials therefor and ease of production thereof. The amino acid pendant type polymer and/or the aminoalcohol pendant type polymer used herein implies a homopolymer, graft copolymer, block copolymer or random copolymer prepared from one or more kinds of such polymerization monomers.

While skin that can be treated by the method for protecting and improving skin of the present invention is not particularly limited, preferred are those generally called damaged skins. Specific examples thereof are, for example, skin damages due to exposure to ultraviolet rays, skin damages due to physical stimuli such as friction and the like, skin damages due to chemicals and the like, degreased skins and the like. The method of the present invention is also effective for conditions milder than those generally called damaged skins so long as there are disordered structures of proteins in surface portions of skin, and free amino groups and carboxyl groups as structural characteristics.

As specific examples of protection or improvement of skin functions by the method for protecting and improving skin of the present invention, there can be mentioned, for example, improvement of moisture retention function, improvement or enhancement of barrier function, normalization of horny layer, improvement of rough skin, improvement of skin crust and the like.

<6> Labeled Compound of the Present Invention

The present invention provides a compound represented by the following Formula (21) and a salt thereof.

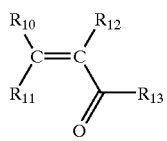

Formula (21)

In the formula, R10 to R12 each independently represent hydrogen atom or an alkyl group having 1–4 carbon atoms, and R13 represents a group having a labeled group.

R10 to R12 each independently represent hydrogen atom or an alkyl group having 1–4 carbon atoms as mentioned above. Specific examples thereof are, for example, hydrogen atom, methyl group, ethyl group, n-propyl group, i-propyl group, n-butyl group, i-butyl group, sec-butyl group, tert-butyl group and the like. Among these, hydrogen atom and methyl group are preferred, since raw materials for the compounds represented by Formula (21) having such groups are widely marketed, and they can readily be obtained.

While the combination of R10 to R12 is not particularly limited, the combination [R10, R11, R12] is preferably [hydrogen atom, hydrogen atom and hydrogen atom] or [hydrogen atom, hydrogen atom and methyl group], because acrylic acid, methacrylic acid or derivatives thereof can be used as raw materials for the compounds having such combinations, and they are widely marketed and can readily be obtained.

In Formula (21), R13 represents a group containing a labeled group. The labeled group used herein is a group enabling identification of a compound containing the group. As the labeled group, there can be mentioned fluorescent labeled group, a coloring group or chromophore, radioactive isotope, enzyme, antibody or the like. Specific examples of the fluorescent labeled group include, for example, dansyl group, stilbene, diphenyl and the like. Examples of the coloring group or chromophore include, for example, nitro group, azo group, azomethines, ketimines, azoxy group and the like. Example of the radioactive isotope include, for example, radioactive isotopes of elements including carbon, hydrogen, nitrogen, oxygen, fluorine, chlorine, bromine, iodine, sulfur, phosphorous and the like. Specific examples of the enzyme are, for example, luminescent enzymes such as luciferase. Specific examples of the antibody include monoclonal antibodies and the like.

R13 may consist solely of a labeled group, or may contain other groups, atomic groups and the like in addition to the labeled group. Examples of the structure containing other groups, atomic groups and the like are, for example, those consisting of an (alkyl) acrylate residue moiety and the labeled group, which are connected with a hydrocarbon group and the like. Among those, preferred are those containing R13 represented as —NH—$(CH_2)_n$—R14 where R14 represents a labeled group and n represents an integer of 2–10. In such a structure, this is because physicochemical properties of the compound of the present invention, for example, water solubility, fat solubility, hydrophilicity, lipophilicity and the like can be controlled by selecting the alkylene group, of which carbon number can easily controlled by selecting a raw material. Furthermore, the compound represented by Formula (21) can be produced by condensing an (alkyl) acrylate or a derivative thereof with a compound represented as $H_2N$—$(CH_2)_n$—R14, and it can be readily performed in a conventional manner. n represents an integer of 2–10, and it is not particularly limited within this range. However, n is more preferably 3–8, particularly preferably 4–7, since such ranges of n are advantageous for the production of the compound represented by Formula (21).

As the labeled group, fluorescent labeled groups are preferred, because fluorescent labeled groups are detected by measuring fluorescence intensity, and measurement of fluorescence intensity can be easily performed.

Among fluorescent labeled groups, dansyl group is preferred, since many reagents for introducing this group are commercially available, and can readily be obtained. Dansyl group is represented by the following Formula (D).

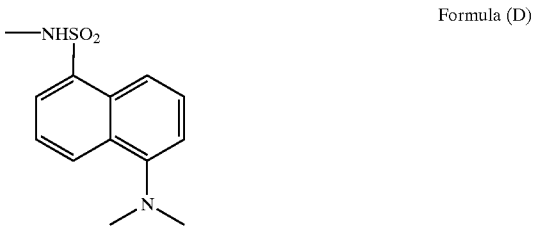

Formula (D)

Among the compounds represented by Formula (21), the compounds represented by the following Formula (22) are particularly preferred.

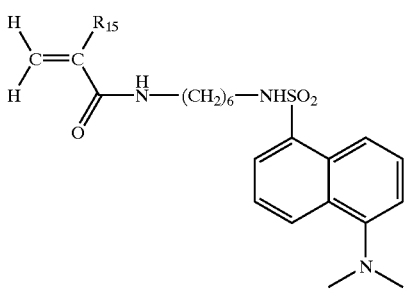

Formula (22)

In the formula, R15 represents hydrogen atom or methyl group.

The method for producing the compounds represented by Formula (21) or salts thereof is not particularly limited, and they can be produced according to common chemical synthesis techniques. Specifically, an (alkyl) acrylateor a derivative thereof can be condensed with a compound from which R13 is derived. The salts of the compounds are not particularly limited.

As will be described below, the compound represented by Formula (21) or a salt thereof is contained in the polymer of the present invention as constituent monomers together with the compound represented by Formula (23) or a salt thereof mentioned below. Therefore, in the polymer of the present invention, the ratio of the compound represented by Formula (21) or a salt thereof to the compound represented by Formula (23) or a salt thereof can be controlled. By defining this ratio, the ratio of the labeled group derived from the compound represented by Formula (21) or a salt thereof to the compound or the salt thereof represented by Formula (23) can be defined. That is, the polymer or salt thereof containing the compound represented by Formula (23) or a salt thereof as constituent monomers can be labeled quantitatively.

A quantitatively labeled polymer can also be obtained by using the compound represented by Formula (21) or a salt thereof as constituent monomers together with one or more compounds other than the compound represented by Formula (23) or a salt thereof. That is, a polymer can be labeled quantitatively by further using the compound represented by Formula (21) or a salt thereof as constituent monomers.

<7> Polymer Containing Labeled Compound of the Present Invention

The polymer of the present invention is a polymer which contains one or more sorts of compounds selected from the compounds represented by Formula (23) or salts thereof together with one or more sorts of compounds selected from the compounds represented by Formula (21) or salts thereof as constituent monomers, or a salt thereof.

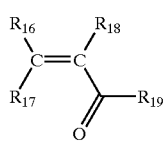

Formula (23)

In the formula, R16 to R18 each independently represent hydrogen atom or an alkyl group having 1–4 carbon atoms, and R19 represents an amino acid residue.

In Formula (23), R16 to R18 each independently represent hydrogen atom or an alkyl group having 1–4 carbon atoms. Specific examples of hydrogen atom and the alkyl group having 1–4 carbon atoms include, for example, hydrogen atom, methyl group, ethyl group, n-propyl group, i-propyl group, n-butyl group, i-butyl group, sec-butyl group, tert-butyl group and the like.

In Formula (23), R19 represents an amino acid residue. The amino acid residue used herein is not particularly limited, and it may be a common amino acid residue. Specific examples thereof include, for example, residues of glutamic acid, alanine, glutamine, lysine, arginine and the like.

The salt of the compound represented by Formula (23) is not particularly limited.

As examples of the compound represented by Formula (23), the compound represented by the aforementioned Formulae (3) to (8) can be mentioned.

A polymer which contains the compound represented by Formula (23) or a salt thereof as constituent monomers or a salt thereof shows effect for protecting or improving body surfaces such as the skin and hair, and is expected to be developed as an ingredient of cosmetics and the like.

In damaged portions of body surfaces including skin and hair, structures of peptides, collagen, keratin and the like are disordered or destroyed, and there are many free amino groups, free carboxyl groups and the like derived from the aforementioned disorder or destruction. Further, the structures of such polymers as mentioned above are characterized by backbone hydrocarbons and amino acid residues contained in their side chains. Therefore, it is estimated that such amino acid residues in the polymers are attached to the free amino groups, free carboxyl groups and the like by affinity so that the body surface conditions should be brought toward better conditions, and the body surfaces should be protected or improved by the adsorption of the polymers to the damaged portions. In order to confirm this estimation, it is necessary to quantitatively determine behaviors of the polymers such as presence and distribution, and hence it is necessary to quantitatively label the polymers.

The polymer of the present invention contains one or more sorts of compounds selected from the compounds represented by Formula (21) orsalts thereof, and one or more sorts of compounds selected from the compounds represented by Formula (23) or salts thereof as constituent monomers. Therefore, in the polymer of the present invention, the ratio of the compound represented by Formula (21) or a salt thereof to the compound represented by Formula (23) or a salt thereof can be controlled. Therefore, by defining this ratio, the ratio of the labeled group derived from the compound represented by Formula (21) or a salt thereof to the compound or the salt thereof represented by Formula (23) can be defined. Thus, the polymer of the present invention can be a quantitatively labeled polymer or salt thereof containing the compound represented by Formula (23) or a salt thereof as constituent monomers.

The content of the compound represented by Formula (21) or a salt thereof in the polymer of the present invention or a salt thereof is not particularly limited so long as it is sufficient for identification of the compound, and it does not degrade the properties of the polymer or a salt thereof which contains the compound represented by Formula (23) or a salt thereof as constituent monomers. Specifically, the molar content of the compound represented by Formula (21) or a salt thereof in the polymer of the present invention is preferably 0.1–20 mol %, more preferably 1–10 mol %, particularly preferably 3–7 mol %.

The production of the polymer of the present invention may be carried out according to a conventional method for producing copolymers. Specifically, the polymer can be obtained by polymerizing one or more kinds of the compounds represented by Formula (21) or salts thereof and one or more kinds of the compounds represented by Formula (23) or salts thereof through solution polymerization or emulsion polymerization in the presence of a polymerization initiator. Salts of the polymer may be formed in a conventional manner, and they may be formed during the polymerization reaction, or formed after the polymerization after isolation of the polymer. Specifically, a salt can be formed by mixing a polymer comprising one or more kinds of the compounds represented by Formula (21) or salts thereof and one or more kinds of the compounds represented by Formula (23) or salts thereof as constituent monomers, and an acid or base with an appropriate ratio in an organic or inorganic solvent.

The polymer of the present invention contains two sorts of compounds mentioned above as constituent monomers, but it may further contain compounds other than those as constituent monomers so long as the advantages of the present invention should not be degraded.

The sequence of the constituent monomers in the polymer of the present invention is not particularly limited so long as the advantages of the present invention should not be degraded. Specifically, it may be a graft copolymer, block copolymer or random copolymer.

<8> Method for Identifying Group Having Amino Acid Residue of the Present Invention The polymer of the present invention has a hydrocarbon chain as a backbone, and amino acid residues in side chains, and labeled quantitatively. Therefore, the polymer of the present invention exhibits higher affinity and adsorption as more amino group exist, and the presence or distribution thereof can be quantitatively determined. Based on these, it is enabled to identify a group having affinity for amino acid residues by using the polymer of the present invention.

The group having affinity for amino acid residues which can be identified by the identification method of the present invention is not particularly limited. Specific examples thereof include, for example, free amino group, free carboxyl group and free thiol group as well as those groups formed when the structures of peptide, collagen, keratin or the like are disordered or destroyed.

<9> Method for Differentiating Body Surface of the Present Invention

At damaged portions of body surfaces including skin and hair, structures of peptides, collagen, keratin etc. are disordered or destroyed, and there are many free amino groups, free carboxyl groups and the like derived from such disorder or destruction. Therefore, when a body surface is treated with the polymer of the present invention, the polymer is less adsorbed to portions of slighter damages, whereas the polymer is more adsorbed to more severely damaged portions. These decrease and increase of the absorption can be determined by the aforementioned method of the present invention. That is, use of the identification method of the present invention for skin as an object of the identification enables quantitative determination of damaged portions and not damaged portion of body surface. This means that the identification method of the present invention can be used for differentiating skin. The term "damage" of body surface used herein include those generally called damages, as well as conditions milder and severer than those.

The body surface that can be differentiated by the differentiation method of the present invention is not particularly limited so long as it is generally called body surface. Specific examples thereof include, for example, skin, hair, nail etc.

The body surface that can be differentiated by the differentiation method of the present invention is not particularly limited as also for the kind of animals so long as it is a body surface of mammal. Specific examples of the mammal include, human, dog, cat, mouse, rat, bovine, sheep and the like.

BEST MODE FOR CARRYING OUT THE INVENTION

Figure 1:
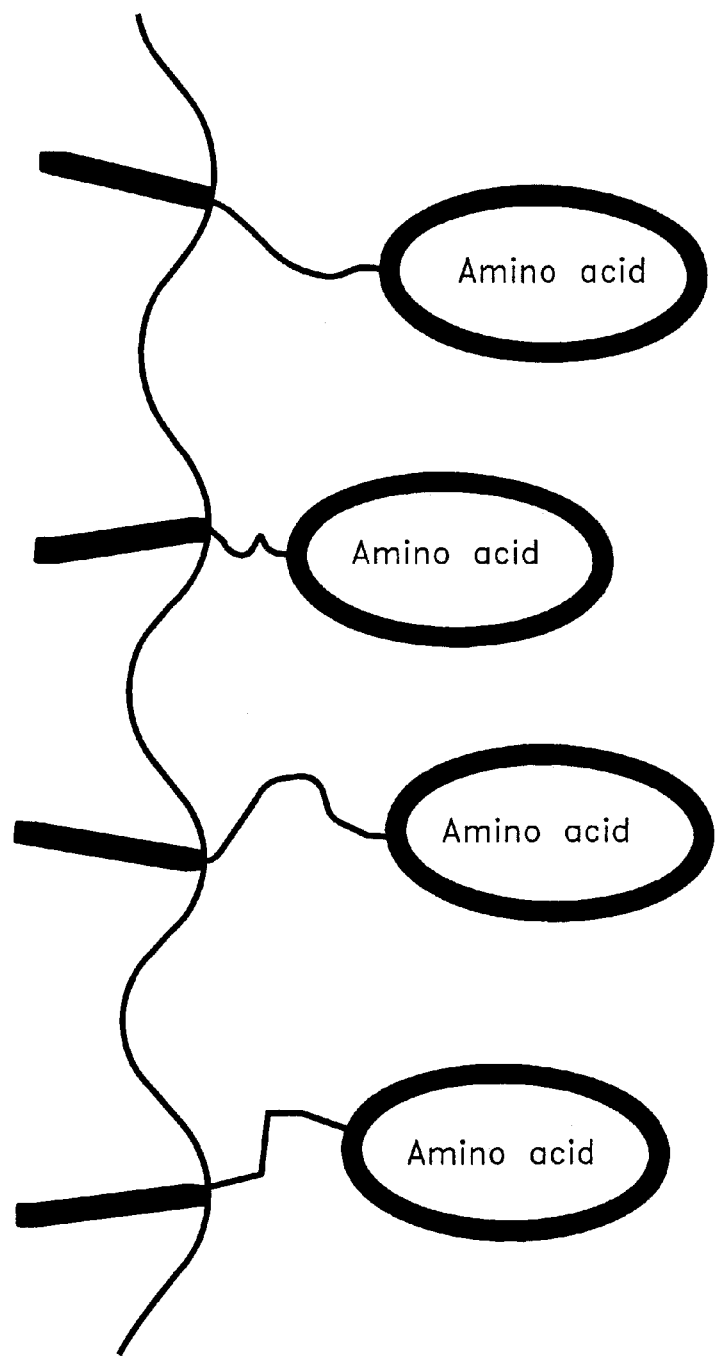
FIG. 1 represents a structure of an amino acid pendant type polymer.

Hereafter, the present invention will be further explained in detail with reference to the following examples. However, the present invention of course is not limited by these examples.

Example 1

Alanine-methacrylamide Polymer (Polymer Comprising Repeating Structures Consisting of Partial Structures Represented by Formula (11))

[1] Alanine-methacrylamide [Compound Represented by Formula (3)]

Potassium carbonate(55.28 g) was dissolved in 200 ml of distilled water, and 17.82 g of D,L-α-alanine was dissolved in the solution. The reaction mixture was added dropwise with 23.00 g of methacryloyl chloride over 20 minutes with vigorous stirring under ice cooling, and further vigorously stirred for about 2 hours. The reaction mixture was adjusted to pH 1–2 with concentrated hydrochloric acid, saturated with sodium chloride, and then extracted with 200 ml of ethyl acetate 3 times. The ethyl acetate layer was dried over anhydrous sodium sulfate, and concentrated. The residue was recrystallized from ethyl acetate, and the obtained crystals were corrected by filtration and dried (white crystals, 19.96 g)

[2] Polymerization

The obtained crystals(8.35 g) were dissolved in 50 ml of distilled water and 50 ml of methanol, and bubbled with nitrogen gas for 30 minutes. Then, 100 mg (0.37 mmol) of potassium persulfate was added to the reaction mixture, and dissolved in it. The reaction mixture was refluxed by heating for 3 hours, then cooled to room temperature, and poured into acetone, so that precipitates were deposited. The supernatant was discarded, and acetone was again added to the precipitates and obtained mixture was stirred. The deposition was collected by filtration and dried to obtain the target polymer (white powder, 6.68 g).

EXAMPLE 2

Glutamine-methacrylamide Polymer (Polymer Comprising Repeating Structures Consisting of Partial Structures Represented by Formula (12))

[1] Glutamine-methacrylamide [Compound Represented by Formula (4)]

Potassium carbonate(34.55 g) was dissolved in 100 ml of distilled water, 7.30 g of L-glutamine was dissolved in the solution, and 20 ml of acetonitrile was further added to the solution. The reaction mixture was added dropwise with 10.45 g of methacryloyl chloride over about 10 minutes with vigorous stirring, and further stirred for about 2 hours. The reaction mixture was adjusted to pH 1–2 with concentrated hydrochloric acid, saturated with sodium chloride, and extracted 2 times with 100 ml of ethyl acetate. The obtained aqueous layer was extracted 3 times with 100 ml of ethyl acetate/isopropanol=1/1. The ethyl acetate/isopropanol layers were combined, concentrated, and purified on a silica gel column (30 g of silica gel, eluted with chloroform/methanol=2/1). The corresponding fractions were collected and concentrated (colorless syrup, 7.47 g)

[2] Polymerization

The obtained syrup(7.47 g) was dissolved in 50 ml of distilled water and 50 ml of methanol, and bubbled with nitrogen gas for 1 hour. Potassium persulfate(100 mg) was added to the reaction mixture, and dissolved in it. The reaction mixture was refluxed by heating for 3 hours, then cooled to room temperature, and poured into isopropanol. The deposition was collected by filtration and dried to obtain the target polymer (white powder, 6.35 g).

EXAMPLE 3

Lysine-methacrylamide polymer (Polymer Comprising Repeating Structures Consisting of Partial Structures Represented by Formula (13) or (14))

[1] Lysine-methacrylamide [Compound Represented by Formula (5) or (6)]

Potassium hydrogencarbonate(5.51 g) was dissolved in 100 ml of distilled water, 9.13 g of lysine hydrochloride was dissolved in the solution, and 80 ml of acetone was further added to the solution. The reaction mixture was added dropwise with 5.23 g of methacryloyl chloride over about 10 minutes with vigorous stirring under ice cooling, and further vigorously stirred for about 2 hours. The reaction mixture was adjusted to pH 1–2 with concentrated hydrochloric acid, and saturated with sodium chloride. The aqueous layer was washed twice with 100 ml of ethyl acetate, and extracted 3 times with 100 ml of ethyl acetate/isopropanol=1/2. The ethyl acetate/isopropanol layers were combined, concentrated to about 50 ml under reduced pressure, added with 500 ml of isopropanol, and again concentrated to about 200 ml. The deposited sodium chloride was removed by filtration, and the filtrate was concentrated (colorless syrup, 5.53 g)

[2] Polymerization

The obtained lysine-mono-methacrylamide hydrochrolide (5.53 g) was dissolved in 50 ml of distilled water, and bubbled with nitrogen gas for 30 minutes. Potassium persulfate(100 mg (0.37 mmol)) was added to the solution, and dissolved in it. The reaction mixture was refluxed by heating for 3 hours, then cooled to room temperature, and poured into acetone, so that precipitates were deposited. The supernatant was discarded, and acetone was again added to the precipitates and obtaiend mixture was stirred. The deposition was collected by filtration and dried to obtain the target polymer (white powder, 4.20 g).

EXAMPLE 4

Arginine-methacrylamide Polymer (Polymer Comprising Repeating Structures Consisting of Partial Structures Represented by Formula (15))

[1] Arginine-methacrylamide [Compound Represented by Formula (7)]

Potassium hydrogencarbonate(27.64 g) was dissolved in 200 ml of distilled water, 21.07 g of arginine hydrochloride was dissolved in the solution, and 80 ml of acetone was further added to the solution. The reaction mixture was added dropwise with 10.46 g of methacryloyl chloride over about 10 minutes with vigorous stirring under ice cooling, and further vigorously stirred for 1 hour. The reaction mixture was adjusted to pH 1 with concentrated hydrochloric acid, and saturated with sodium chloride. The aqueous layer was washed 3 times with 300 ml of ethyl acetate, and extracted 3 times with 200 ml of ethyl acetate/isopropanol =1/1. The ethyl acetate/isopropanol layers were combined, concentrated to about 100 ml under reduced pressure, added with 400 ml of isopropanol, and again concentrated to about 200 ml. The deposited sodium chloride was removed by filtration, and the filtrate was concentrated (colorless syrup, 21.80 g)

[2] Polymerization

The obtained arginine-mono-methacrylamide hydrochloride(4.84 g) was dissolved in 40 ml of distilled water, and bubbled with nitrogen gas for 1 hour. Potassium persulfate(60 mg) was added to the solution, and dissolved in it. The reaction mixture was refluxed by heating for 3 hours, then cooled to room temperature, and poured into acetone, so that precipitates were deposited. The supernatant was discarded, and acetone was again added to the precipitates and obtained mixture was stirred. The deposition was collected by filtration and dried to obtain the target polymer (white powder, 3.05 g).

EXAMPLE 5

Alanine-methacrylamide/Arginine-methacrylamide (=7:3) Copolymer (Polymer Comprising Repeating Structures Consisting of Partial Structures Represented by Formula (16))

Arginine-methacrylamide hydrochloride(10.53 g) and 13.90 g of the aforementioned alanine-methacrylamide were dissolved in 100 ml of distilled water, and bubbled with nitrogen gas for 1 hour. Potassium persulfate(250 mg) was added to the solution, and dissolved in it. The reaction mixture was refluxed by heating for 3 hours, then cooled to room temperature, and poured into acetone, so that precipitates were deposited. The supernatant was discarded, and acetone was again added to the precipitates and obtained mixture was stirred. The deposition was collected by filtration and dried to obtain the target polymer (white powder, 20.90 g).

EXAMPLE 6

Ethyltrimethylammonium Chloride-methacrylic Acid Ester Polymer (Polymer Comprising Repeating Structures Consisting of Partial Structures Represented by Formula (17))

A choline was produced in a conventional manner by using trimethylamine and ethylene oxide as raw materials, and this coline was condensed with methacrylic acid in the presence of base catalyst to obtain ethyltrimethylammonium chloride-methacrylic acid ester [a compound represented by Formula (8)].

Subsequently, the title polymer was obtained in the same manner as in the polymerization described in Examples 1–4.

EXAMPLE 7

Evaluation of Skin Function Protection/Improvement Effects of the Polymer of the Present Invention It was confirmed that the polymer of the present invention could protect and improve the proper skin functions by using SDS-damaged skin and ultraviolet ray-damaged skin.

The alanine-methacrylamide polymer [polymer containing a compound represented by Formula (3) as the constituent monomers](1 g) was added to 100 ml of water, and obtained mixture was stirred sufficiently, added portionwise with 0.5 N aqueous sodium hydroxide to be adjusted to about pH 7 to obtain a sample for administration.

[1] Evaluation of Improvement Effect Using SDS-damaged Skin

In this experiment, change of transepidermal water loss, i.e., change of horny layer moisture content, was used as an index for evaluation of the skin function protection and improvement effects.

A 5% SDS aqueous solution was applied to back skin (50 mm×30 mm) of hairless mice (male, body weight: 25–30 g), each of which group consists of ten mice, twice a day in an amount of 0.1 ml for each application for 5 consecutive days, and the solution was not applied next 2 days. This procedure was repeated for the period of the first day to 19th day to obtain damaged skin. The sample was administered by applying the sample solution in an amount of 0.1 ml for each application on each of 9 days, i.e., 8th day to 12th day and 15th day to 18th day. The trasnepidermal water loss (TEWL) was measured on the first, 8th, 10th, 12th, 15th, 17th and 19th days. The results are shown in the following Table 1. From the results, it was confirmed that the skin functions were improved by the treatment with the described polymer. That is, it was confirmed that the polymer of the present invention improved the skin function. Moreover, it was found that the polymer of the present invention was particularly effective for damaged skin caused by a chemical irritant represented by SDS-damaged skin.

TABLE 1

| Day | 1 | 8 | 10 | 12 | 15 | 17 | 19 |
|---|---|---|---|---|---|---|---|
| Polymer (3) | 10 | 13.7 | 14.9 | 20.0 | 10.0 | 11.1 | 11.0 |
| No treatment | 10 | 17.5 | 23.0 | 25.0 | 21.0 | 20.5 | 18.3 |

[2] Evaluation of Improvement Effect Using SDS-damaged Skin

A 5% SDS aqueous solution was applied to back skin (50 mm×30 mm) of hairless mice (male, body weight: 25–30 g), each of which group consists of ten mice, twice a day in an amount of 0.1 ml for each application on each of 9 days, i.e., 8th day to 12th day and 15th day to 18th day to obtained damaged skin. The sample was administered by applying the sample solution in an amount of 0.1 ml for each application on each of 14 days, i.e., the first to 5th day, 8th day to 12th day, and 15th day to 18th day. The trasnepidermal water loss (TEWL) was measured on the first, 8th, 10th, 12th, 15th, 17th and 19th days. The results are shown in the following Table 2. From the results, it was confirmed that the skin functions were preventively protected by the treatment with the described polymer. That is, it was confirmed that the polymer of the present invention protected the skin function. Moreover, it was found that the polymer of the present invention was particularly effective for damaged skin caused by a chemical irritant represented by SDS-damaged skin.

TABLE 2

| Day | 1 | 8 | 10 | 12 | 15 | 17 | 19 |
|---|---|---|---|---|---|---|---|
| Polymer (3) | 10 | 12.5 | 17.3 | 21.0 | 14.4 | 16.8 | 16.9 |
| No treatment | 10 | 16.5 | 22.0 | 24.5 | 23.0 | 21.0 | 19.0 |

[3] Evaluation of Improvement Effect Using UV Ray-damaged Skin

Back skins (50 mm×30 mm) of hairless mice (male, body weight: 25–30 g), each of which group consists of ten mice, were irradiated with an ultraviolet ray of 3 MED on the 5th day to obtain damaged skin.

The sample was administered by applying the sample solution in an amount of 0.1 ml for each application on each of 4 days, i.e., the 8th to 11th day.

The trasnepidermal water loss (TEWL) was measured on the first and 8th to 12th days. The results are shown in the following Table 3.

TABLE 3

| Day | 1 | 8 | 9 | 10 | 11 | 12 |
|---|---|---|---|---|---|---|
| Polymer (3) | 10 | 23.7 | 32.2 | 23.6 | 16.8 | 16.3 |
| No treatment | 10 | 38.4 | 41.1 | 41.1 | 35.0 | 30.0 |

From the results, it was confirmed that the skin functions were improved by the treatment with the described polymer. That is, it was confirmed that the polymer of the present invention improved skin. Moreover, it was found that the method for protecting or improving skin of the present invention was particularly effective for damaged skin caused by an ultraviolet ray.

[4] Evaluation of Preventive Protection Effect Using UV Ray-damaged Skin

Backskins (50 mm×30 mm) of hairless mice (male, body weight: 25–30 g), each of which group consists of ten mice, were irradiated with an ultraviolet ray of 3 MED on the 5th day to obtain damaged skin.

The sample was administered by applying the sample solution in an amount of 0.1 ml for each application on each of 8 days, i.e., the first to 4th days and 8th to 11th days.

The trasnepidermal water loss (TEWL) was measured on the first and 8th to 12th days. The results are shown in the following Table 4.

TABLE 4

| Day | 1 | 8 | 9 | 10 | 11 | 12 |
|---|---|---|---|---|---|---|
| Polymer (3) | 10 | 33.7 | 29.7 | 19.1 | 17.0 | 15.9 |
| No treatment | 10 | 47.8 | 42.1 | 35.0 | 33.5 | 31.0 |

From the results, it was confirmed that the skin function was preventively protected by the treatment with the described polymer. That is, it was confirmed that the polymer of the present invention protected the skin function. Moreover, it was found that the method for protecting or improving skin of the present invention was also effective for damaged skin caused by an ultraviolet ray.

[5] Effect of the Method for Protecting or Improving Skin of the Present Invention A 1% aqueous solution of alanine-methacrylamide polymer was applied to dry skin of panels 3 times a day for 2 weeks, and improvement degree was voluntarily reported by the panels. For control, a conventional treatment, treatment with 1% aqueous solution of a moisturizer, propylene glycol, was used (14 panels for each, 28 panels in total). The results are shown in Table 5.

TABLE 5

|  | Improved | Slightly improved | No change | Slightly aggravated | Aggravated |
|---|---|---|---|---|---|
| Polymer (3) | 4 | 7 | 3 | 0 | 0 |
| Propylene glycol | 0 | 6 | 5 | 3 | 0 |

In 11 panels out of 14, the condition was improved or slightly improved, and hence the polymer was effective with an improvement ratio of about 80%. That is, it was confirmed that the method for protecting and improving skin according to the present invention could provide more effective protection and improvement compared with the conventional treatment.

EXAMPLE 8

Cosmetic Lotion

Cosmetic lotions were prepared according to the following prescription. That is, the ingredients were dissolved by stirring to obtain the cosmetic lotions. These cosmetic lotions all exhibited skin protection effect, i.e., marked effectiveness, in particular, for persons having skin with reduced moisture retention ability due to skin damages such as atopic dermatitis.

| Glycerin | 5 parts by weight |
|---|---|
| 1,3-Butanediol | 5 parts by weight |
| Ethanol | 10 parts by weight |
| Polymer* | 0.1 parts by weight |
| Methylparaben | 0.2 parts by weight |
| Sodium hyaluronate | 0.1 parts by weight |
| Water | 79.6 parts by weight |

*Details are shown in Table 6.

TABLE 6

|  | Polymer | Effect on atopic dermatitis |
|---|---|---|
| Test Example 1 | Polymer of Example 1 | Good effect |
| Test Example 2 | Polymer of Example 2 | Good effect |
| Test Example 3 | Polymer of Example 3 | Good effect |
| Test Example 4 | Polymer of Example 4 | Good effect |
| Test Example 5 | Polymer of Example 5 | Good effect |
| Test Example 6 | Polymer of Example 6 | Good effect |
| Comparative Example 1 | Poly(sodium acrylate) | No effect |
| Comparative Example 2 | Sodium glutamate | No effect |
| Control | Water | No effect |

EXAMPLE 9

Moisturizing Cream

Moisturizing creams (cosmetic creams) were prepared according to the following prescription. That is, the following Compositions A, B and C were heated to 80° C., Composition A was dispersed in Composition B by stirring, and Composition C was gradually added to the dispersion to obtain an emulsion. The emulsion was cooled with stirring to obtain a moisturizing cream.

| A. | |
|---|---|
| Triglycerol diisostearate | 2% by weight |
| Diglycerol monooleate | 3% by weight |
| 1,3-Butylene glycol | 5% by weight |
| Glycerin | 3% by weight |
| Cetanol | 5% by weight |
| Solid paraffin | 3% by weight |
| Methylparaben | 0.2% by weight |
| B. | |
| Liquid paraffin | 10% by weight |
| Squalane | 10% by weight |
| C. | |
| Polymer** | 0.5% by weight |
| Sodium trehalose sulfate | 0.5% by weight |
| Water | 57.8% by weight |

**Details are shown in Table 7.

TABLE 7

|  | Polymer | Effect on atopic dermatitis |
|---|---|---|
| Test Example 7 | Polymer of Example 1 | Good effect |
| Test Example 8 | Polymer of Example 2 | Good effect |
| Test Example 9 | Polymer of Example 3 | Good effect |
| Test Example 10 | Polymer of Example 4 | Good effect |
| Test Example 11 | Polymer of Example 5 | Good effect |
| Test Example 12 | Polymer of Example 6 | Good effect |
| Comparative Example 3 | Poly(sodium acrylate) | No effect |
| Comparative Example 4 | Sodium glutamate | No effect |
| Control | Water | No effect |

EXAMPLE 10

Cream

Creams (pharmaceutical composition for topical to skin) were prepared according to the following prescription. That is, the following Compositions A, B and C were heated to 80° C., Composition A was dispersed in Composition B by stirring, and Composition C was gradually added to the dispersion to obtain an emulsion. The emulsion was cooled with stirring to obtain a cream. The creams showed effect for exerting the efficacy of the steroid more efficiently.

| A. | |
|---|---|
| Triglycerol diisostearate | 2% by weight |
| Diglycerol monooleate | 3% by weight |
| 1,3-Butylene glycol | 5% by weight |
| Glycerin | 3% by weight |
| Cetanol | 5% by weight |
| Solid paraffin | 3% by weight |
| Methylparaben | 0.2% by weight |
| B. | |
| Liquid paraffin | 10% by weight |
| Squalane | 10% by weight |
| Dexamethasone | 1% by weight |
| C. | |
| Polymer*** | 0.5% by weight |
| Sodium trehalose sulfate | 0.5% by weight |
| Water | 56.8% by weight |

***Details are shown in Table 8.

TABLE 8

| | Polymer | Effect on atopic dermatitis |
|---|---|---|
| Test Example 13 | Polymer of Example 1 | Good effect |
| Test Example 14 | Polymer of Example 2 | Good effect |
| Test Example 15 | Polymer of Example 3 | Good effect |
| Test Example 16 | Polymer of Example 4 | Good effect |
| Test Example 17 | Polymer of Example 5 | Good effect |
| Test Example 18 | Polymer of Example 6 | Good effect |
| Comparative Example 5 | Poly(sodium acrylate) | No effect |
| Comparative Example 6 | Sodium glutamate | No effect |
| Control | Water | No effect |

EXAMPLE 11

[1] Preparation of Compound Represented by Formula (5) and Compound Represented by Formula (6)

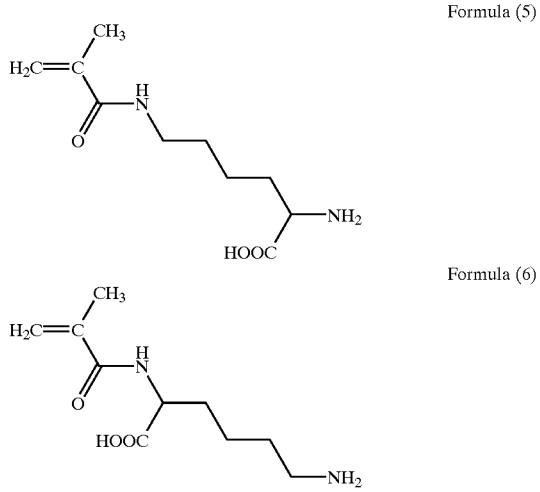

To a 500 ml-reaction-vessel, lysine hydrochloride (78.62 g; 0.430mol) and 200 ml of distilled water were added, and vigorously stirred under ice cooling. Then, the reaction mixture was adjusted to pH 8.0 by adding a small amount of aqueous sodium hydroxide (about 50 wt/v %). Further, methacryloyl chloride (37.50 g; 0.359 mol) and aqueous sodium hydroxide were simultaneously added dropwise to the mixture over about 15 minutes with vigorous stirring, while the mixture in the reaction vessel was kept at pH 8.0. After the addition was completed, the mixture was returned to room temperature, and stirred vigorously for 30 minutes. The reaction residue was adjusted to pH 2–3 by adding concentrated hydrochloric acid (about 30 ml), and subjected to liquid-liquid extraction (washing) with 300 ml of ethyl acetate twice. The aqueous layer was separated, neutralized to pH 7.0 with aqueous sodium hydroxide, added p-methoxyphenol (about 50 mg) and n-butanol (about 150 ml), and concentrated under reduced pressure to a residual amount of about 270 g. Further, the residue was added 1.4 L of isopropanol, obtained mixture was stirred vigorously for about 90 minutes, and then left stand at 5° C. for about 90 minutes. The deposited insoluble substances were removed by filtration, and the filtrate was added p-methoxyphenol (about 50 mg), and concentrated to a residual weight of about 700 g. The procedure comprising addition of isopropanol (about 500 ml) and concentration was repeated twice. After a while, crystals were deposited, and they were left overnight at 5° C. Then, the crystals were collected by filtration, washed with isopropanol, and dried to obtain about 40 g of the compound represented by Formula (5) and the compound represented by Formula (6) as white powder. These had higher purity and lower moisture content compared with the compound obtained in Comparative Example mentioned below. This was considered to be caused by the crystallization.

[2] Comparative Example for Preparation of Hydrochlorides of Compound Represented by Formula (5) and Compound Represented by Formula (6)

Preparation of Hydrochlorides of Compound Represented by Formula (5) and Compound Represented by Formula (6)

To a 500 ml-reaction-vessel, lysine hydrochloride (78.62 g; 0.430 mol) and 200 ml of distilled water were added, and vigorously stirred under ice cooling. Then, the reaction mixture was adjusted to pH 8.0 by adding a small amount of aqueous sodium hydroxide (about 50 wt/v %). Further, methacryloyl chloride (37.50 g; 0.359 mol) and aqueous sodium hydroxide were simultaneously added dropwise to the mixture over about 15 minutes with vigorous stirring, while the mixture in the reaction vessel was kept at pH 8.0. After the addition was completed, the mixture was returned to room temperature, and stirred vigorously for 30 minutes. The reaction residue was adjusted to pH 2–3 by adding concentrated hydrochloric acid (about 30 ml), and saturated with sodium chloride. The mixture was washed with ethyl acetate (about 300 ml) 3 times, and the aqueous layer was extracted with isopropanol. The isopropanol layer was once concentrated, added isopropanol again, and concentrated. The deposition was removed by filtration, and the filtrate was concentrated and dried to obtain hydrochlorides of the compound represented by Formula (5) and the compound represented by Formula (6) as oil.

EXAMPLE 12

Preparation of Fluorescence-labeled Polymer

Each of the polymers prepared in Examples 1–6 was labeled with fluorescent dansyl group.

A compound introduced with dansyl group, which was represented by Formula (20), was added to the original monomer for polymer at a ratio of about 1/50, and polymerized to prepare a fluorescence-labeled polymer.

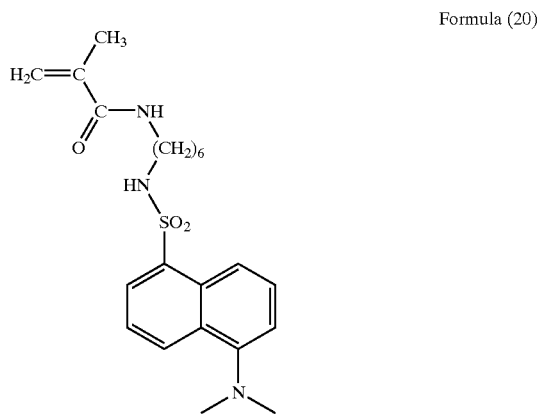

(1) Preparation of Compound Represented by Formula (20) (Dansylated Hexamethylenediamine-methacrylamide): fluorescence-labeled Monomer Hexamethylenediamine(4.33 g) was dissolved in 50 ml of pyridine, and added dropwise with 2.33 g of dansyl chloride dissolved in 50 ml of acetone over about 3 hours. Then, the mixture was stirred for 1 hour, the solvent was evaporated, and the residue was purified by silica gel column chromatography (eluted with chloroform/methanol=9/1–6/4). The corresponding fractions were collected and concentrated (yield: 2.54 g)

The aforementioned compound(2.5 g) was dissolved in 50 ml of dichloromethane, added 0.17 g of dimethylaminopyridine and 0.84 g of methacrylic acid, and stirred sufficiently. The reaction mixture was added with 1.77 g of dicyclohexylcarbodiimide, and stirred overnight. Then, the solvent was evaporated, and the residue was purified by silica gel column chromatography (eluted with chloroform/methanol=10/0–9/1), and the corresponding fractions were collected and concentrated to obtain target compound (yield: 2.85 g).

(2) Synthesis of Fluorescence-labeled Polymer

Each of the various amino acid-bonded methacrylic acid monomers and the fluorescence-labeled monomer in an amount of 2 mol % of the methacrylic acid monomer were dissolved in water/methanol=1/1, and bubbled with nitrogen gas for 1 hour. This solution was added potassium persulfate as a polymerization initiator in an amount of about 1/50 mol equivalents, and refluxed by heating for 3 hours with nitrogen gas bubbling. The reaction mixture was poured into isopropanol or acetone to deposit precipitates. The supernatant was removed by decantation, and acetone was added to the precipitates, and stirred vigorously. The produced precipitates (powdered form) were collected by filtration, washed with acetone, and dried to obtain the target polymer.

PREPARATION EXAMPLE 1

Synthesis of Fluorescence-labeled Compound of Alanine-methacrylamide Polymer [fluorescence-labeled Compound of the Polymer of Example 1]

Alanine-methacrylamide(3.92 g) and 0.208 g of the fluorescence-labeled monomer was dissolved in a mixed solvent of 20 ml of water and 20 ml of methanol, and bubbled with nitrogen gas for 1 hour. Potassium persulfate (0.120 g) was added to and dissolved in this solution, and the solution was refluxed by heating for 3 hours while maintaining nitrogen gas bubbling. The reaction mixture was poured into acetone to form precipitates. The supernatant was removed by decantation, and acetone was added again to the precipitates, and obtained mixture was stirred vigorously. The produced precipitates (powdered form) were collected by filtration, washed with acetone, and dried to obtain the target polymer.

PREPARATION EXAMPLE 2

Synthesis of Fluorescence-labeled Compound of Glutamine-methacrylamide Polymer [Fluorescence-labeled Compound of the Polymer of Example 2]

Glutamine-methacrylamide(3.29 g) and 0.129 g of the fluorescence-labeled monomer was dissolved in a mixed solvent of 20 ml of water and 20 ml of methanol, and bubbled with nitrogen gas for 1 hour. Potassium persulfate (0.075 g) was added to and dissolved in this solution, and the solution was refluxed by heating for 3 hours while maintaining nitrogen gas bubbling. The reaction mixture was poured into isopropanol to form precipitates. The supernatant was removed by decantation, and acetone was added again to the precipitates, and obtained mixture was stirred vigorously. The produced precipitates (powdered form) were collected by filtration, washed with acetone, and dried to obtain the target polymer.

PREPARATION EXAMPLE 3

Synthesis of Fluorescence-labeled Compound of Lysine-methacrylamide Polymer [Fluorescence-labeled Compound of the Polymer of Example 3]

Lysine-methacrylamide(2.26 g) was dissolved in 30 ml of water, added 0.089 g of the fluorescence-labeled monomer dissolved in 30 ml of methanol, and bubbled with nitrogen gas for 1 hour. Potassium persulfate(0.030 g) was added to and dissolved in this solution, and the solution was refluxed by heating for 3 hours while maintaining nitrogen gas bubbling. The reaction mixture was poured into isopropanol to form precipitates. The supernatant was removed by decantation, and acetone was added again to the precipitates, and obtained mixture was stirred vigorously. The produced precipitates (powdered form) were collected by filtration, washed with acetone, and dried to obtain the target polymer.

PREPARATION EXAMPLE 4

Synthesis of Fluorescence-labeled Compound of Arginine-methacrylamide Polymer [Fluorescence-labeled Compound of the Polymer of Example 4]

Arginine-methacrylamide(2.56 g) was dissolved in 30 ml of water, added 0.089 g of the fluorescence-labeled monomer dissolved in 30 ml of methanol, and bubbled with nitrogen gas for 1 hour. Potassium persulfate(0.032 g) was added to and dissolved in this solution, and the solution was refluxed by heating for 3 hours while maintaining nitrogen gas bubbling. The reaction mixture was poured into isopropanol to form precipitates. The supernatant was removed by decantation, and acetone was added again to the precipitates, and obtained mixture was stirred vigorously. The produced precipitates (powdered form) were collected by filtration, washed with acetone, and dried to obtain the target polymer.

PREPARATION EXAMPLE 5

Synthesis of Fluorescence-labeled Compound of Alanine-methacrylamide/Arginine-methacrylamide (7/3) Copolymer [Fluorescence-labeled Compound of the Copolymer of Example 5]

Alanine-methacrylamide(2.20 g) and 1.67 g of arginine-methacrylamide hydrochloride were dissolved in 15 ml of water, added 0.167 g of the fluorescence-labeled monomer dissolved in 15 ml of methanol, and bubbled with nitrogen gas for 1 hour. Potassium persulfate(0.060 g) was added to and dissolved in this solution, and the solution was refluxed by heating for 3 hours while maintaining nitrogen gas bubbling. The reaction mixture was poured into isopropanol to form precipitates. The supernatant was removed by decantation, and acetone was added again to the precipitates, and obtained mixture was stirred vigorously. The produced precipitates (powdered form) were collected by filtration, washed with acetone, and dried to obtain the target polymer.

PREPARATION EXAMPLE 6

Synthesis of Fluorescence-labeled Compound of Ethyltrimethylammonium Chloride/Methacrylic Acid Ester Polymer [Fluorescence-labeled Compound of the Polymer of Example 6]

Ethyltrimethylammonium chloride/methacrylic acid ester (4.15 g) was dissolved in 30 ml of water, added 0.167 g of the fluorescence-labeled monomer dissolved in 30 ml of methanol, and bubbled with nitrogen gas for 1 hour. Potassium persulfate(0.050 g) was added to and dissolved in this solution, and the solution was refluxed by heating for 3 hours while maintaining nitrogen gas bubbling. The reaction mixture was poured into isopropanol to form precipitates. The supernatant was removed by decantation, and acetone was added again to the precipitates, and obtained mixture was stirred vigorously. The produced precipitates (powdered form) were collected by filtration, washed with acetone, and dried to obtain the target polymer.

PREPARATION EXAMPLE 7

Synthesis of Fluorescence-labeled Compound of Alanine-methacrylamide/Arginine-methacrylamide (=9/1) Copolymer

PREPARATION EXAMPLE 8

Synthesis of Fluorescence-labeled Compound of Alanine-methacrylamide/Arginine-methacrylamide (=8/2) Copolymer

PREPARATION EXAMPLE 9

Synthesis of Fluorescence-labeled Compound of Alanine-methacrylamide/Arginine-methacrylamide (=5/5) Copolymer As for Preparation Examples 7–9, the polymers were prepared in accordance with the method described in Preparation Example 5 by changing the ratio of the raw materials, the compound represented by Formula (3) and the compound represented by Formula (7).

EXAMPLE 13

Evaluation of Skin Adsorptivity

The skin adsorptivity of the polymers was evaluated using the fluorescence-labeled polymers produced in the aforementioned examples.
(1) Preparation of Skin Horny Layer for Evaluation of Adsorptivity As skin samples used for the evaluation, three sorts of samples, non-treated, SDS-treated, and ultraviolet ray-radiated skins, were produced.

1. Non-treated Horny Layer

Exfoliated back skin (20 mm×20 mm) of hairless mice (male, body weight: 25–30 g) was treated with dispase to extract the skin. This skin was treated with trypsin in 0.25% phosphate buffer at 37° C. for 1 hour to extract a horny layer, and 10 mm×10 mm of horny layer was applied to slide glass for fluorescence microscopes, and air-dried for 24 hours.

2. SDS-treated Horny Layer

Five percent aqueous solution of SDS(0.1 ml) was applied to back skin (50 mm×30 mm) of hairless mice (male, body weight: 25–30 g) once a day for 3 days. Exfoliated back skin (20 mm×20 mm) of them was treated with dispase to extract the skin. This skin was treated with trypsin in 0.25% phosphate buffer at 37° C. for 1 hour to extract a horny layer, and 10 mm×10 mm of horny layer was applied to slide glass for fluorescence microscopes, and air-dried for 24 hours.

3. Ultraviolet Ray-damaged Horny Layer

An ultraviolet ray of 3 MED was irradiated once on back skin (50 mm×30 mm) of hairless mice (male, body weight: 25–30 g). Exfoliated back skin (20 mm×20 mm) of them was treated with dispase to extract the skin. This skin was treated with trypsin in 0.25% phosphate buffer at 37° C. for 1 hour to extract a horny layer, and 10 mm×10 mm of horny layer was applied to slide glass for fluorescence microscopes, and air-dried for 24 hours.

(2) Evaluation of Adsorptivity of Fluorescence-labeled Alanine-methacrylamide Polymer Compared With Ultraviolet Ray-damaged Horny Layer (i) First, derived was a calibration equation for fluorescence intensity required for calculating horny layer adsorptivity, which will be explained below.

The ultraviolet ray-damaged horny layer was treated with the fluorescence-labeled compound, and fluorescence of the treated horny layer was measured to determine the correlation of the fluorescence intensity and the applied amount of sample.

(a) A piece of slide glass having the ultraviolet ray-damaged horny layer was immersed in 50 ml of water for 10 minutes, and then air-dried for 30 minutes. By using slide glass as a blank, fluorescence intensity of the horny layer was measured (blank, $A_B$).

(b) Ten micro-liter of 0.05 wt % solution of each fluorescence-labeled polymer in water containing 30% ethanol was applied, and dried for 30 minutes. Then, fluorescence intensity was measured ($A_{0.05}$: Ex. 331 nm, Em. 505 nm).

(c) Then, 10 μl of 0.2 wt % solution of each fluorescence-labeled polymer in water containing 30% ethanol was further applied, and dried for 30minutes. Then, fluorescence intensity was measured ($A_{0.25}$: Ex. 331 nm, Em. 505 nm).

(d) Finally, 10 μl of 0.5 wt % solution of each fluorescence-labeled polymer in water containing 30% ethanol was applied, and dried for 30 minutes. Then, fluorescence intensity was measured ($A_{0.75}$: Ex. 331 nm, Em. 505 nm).

The fluorescence intensity at each concentration was calculated as follows.

---

Fluorescence Intensity at 0.05 wt % =
$A_{0.05} - A_B = 389 - 242 = 147$
Fluorescence Intensity at 0.25 wt % =
$A_{0.25} - A_B = 674 - 242 = 432$
Fluorescence Intensity at 0.75 wt % =
$A_{0.75} - A_B = 1648 - 242 = 1406$

---

Then, based on the fluorescence intensity, (X, Y)=(0, 0), (0.05, 147), (0.25, 432) and (0.75, 1406) were processed by the least square method to defined the calibration equation: Y=1843.801X+12.252. Based on the calibration equation, correlation of the fluorescence intensity and the applied amount of the sample was obtained.

(ii) Then, apparent adsorption strength ($A_1$) and apparent adhering strength ($A_0$) were measured.

The "apparent adsorption strength" used herein means a degree of absorption of polymer to skin. The "apparent adsorption strength" used herein is defined to be a sum of the following two kinds of adsorptivities:

(a) adsorptivity caused by chemical affinity between the polymer and skin (herein referred to as "true adsorptivity"), and (b) physical adsorptivity of the polymer itself (herein referred to as "adhering strength").

Therefore, there is the following correlation:

True adsorption strength ($A^*$)=Apparent adsorption strength ($A_1$)−Adhering strength ($A_0$)

A piece of slide glass having a horny layer was immersed in 50 ml of water for 10 minutes, and then air-dried for 30 minutes. By using this slide glass as a blank, fluorescence intensity of the horny layer was measured (blank, $A_B$).

Further, 10 μl of 5 wt % solution of each fluorescence-labeled polymer in water containing 30% ethanol was applied to the slide glass, and air-dried for 30 minutes. The slide glass was immersed in 50 ml of water again for 10 minutes, and air-dried for 30 minutes. Then, fluorescence intensity was measured ($A_S$: Ex. 331 nm, Em. 505 nm).

The apparent absorption strength $A_1$ was calculated in accordance with an equation:

$$A_1 = A_S - A_B.$$

$$A_1 = A_S - A_B = 113.7$$

Adhering strength ($A_0$)

Fluorescence intensity of slide glass was determined (blank, $A_B$).

Further, 10 μl of 5 wt % solution of each fluorescence-labeled polymer in water containing 30% ethanol was applied, and air-dried for 30 minutes. The slide glass was immersed in 50 ml of water again for 10 minutes, and air-dried for 30 minutes. Then, fluorescence intensity was measured ($A_H$: Ex. 331 nm, Em. 505 nm).

The adhering strength $A_0$ was calculated in accordance with an equation:

$$A_0 = A_H - A_B.$$

$$A_0 = A_H - A_B = 0.2$$

The true adsorption strength ($A^*$) was calculated from the apparent adsorption strength and adhering strength obtained as described above according the following equation:

$$\text{True adsorption strength } (A^*) = \text{Apparent adsorption strength } (A_1) - \text{Adhering strength } (A_0)$$
$$= 113.7 - 0.2 = 113.5$$

Then, adsorption amount was calculated from the obtained true adsorption strength using the calibration curve defined above.

$$113.5 = 1843.801X + 12.252$$

$$X = 0.0549$$

Finally, horny layer adsorption ratio was calculated as follows:

$$\text{Horny layer adsorption ratio} = \text{Adsorption ratio } (\%)/5(\%) \times 100$$
$$= 0.0549/5 \times 100$$
$$= 1.098(\%)$$

The horny layer adsorption ratio was calculated by repeating the above procedure 5 times, and average of the obtained values was calculated to be 1.10 (%). This value was used as an index of the horny layer adsorption ratio of the polymer. As also for other fluorescence-labeled compounds, averages of horny layer adsorption ratio values from 5 experiments were calculated. The same procedure was repeated as also for the SDS-treated horny layer and the non-treated horny layer to obtain horny layer adsorption ratios for them (averages of 5 experiments). The results are shown in Table 9.

TABLE 9

| Labeled Compound | 1 | 2 | 3 | 4 | 5 |
|---|---|---|---|---|---|
| Non-treated | 0.75 | 1.10 | 1.00 | 0 | 1.10 |
| SDS-treated | 1.38 | 1.50 | 2.10 | 1.80 | N.E. |
| UV-damaged | 1.10 | 1.30 | 3.00 | 2.00 | 1.40 |

N.E.: Not evaluated

The numbers of the labeled compounds used in Table 9 indicate the following compounds.

Labeled Compound 1: Alanine-methacrylamide polymer,
Labeled Compound 2: Glutamine-methacrylamide polymer,
Labeled Compound 3: Lysine-methacrylamide polymer,
Labeled Compound 4: Alanine-methacrylamide/arginine-methacrylamide (=7:3) copolymer,
Labeled Compound 5: Ethyltrimethylammonium chloride/methacrylic acid ester polymer It was confirmed that the polymers showed stronger chemical affinity for damaged skin such as the SDS-treated horny layer and the ultraviolet ray-damaged skin compared with the non-treated horny layer. That is, it was confirmed that the group having affinity for amino groups and/or the group having affinity for carboxyl group, which are the characteristic of the polymers, were more strongly attracted by affinity to portions of disordered skin structures, and restored them.

As for the copolymers obtained in Example 12, since the ratio of the raw materials, the compound represented by Formula (22) and the compound represented by Formula (23), was controlled, the constituent monomer content of the compound represented by Formula (22) was defined. That is, the copolymers obtained in Example 12 contained a definite amount of labeled groups, because they contained the compound represented by Formula (22). Therefore, behavior of the copolymers can be determined quantitatively.

From the results shown in Table 9, it can be seen that a larger amount of the polymers are adsorbed to the SDS-treated horny layer and the ultraviolet ray-damaged horny layer compared with the non-treated horny layer. This is because the SDS-treated horny layer and the ultraviolet ray-damaged horny layer contain more disordered or destroyed structures of peptides, collagen and keratin, and more groups having affinity for amino acid residues containing free amino groups and carboxyl groups originating from the disorder or destruction compared with the non-treated horny layer, and they attracted by affinity and adsorbed to the amino acid residues contained in the side chains of the copolymers obtained in Example 12. That is, by using the copolymer molecules obtained in Example 12, it becomes possible to identify groups having affinity for amino acid residues including free amino groups and free carboxyl groups.

Furthermore, if a body surface is treated with the copolymers obtained in Example 12, larger amounts of these copolymers will be adsorbed to damaged sites of the body surface. Therefore, it becomes possible to differentiate body surfaces by tracing the copolymers to identify groups having affinity for amino acid residues.

EXAMPLE 14

Evaluation of Adsorptivity for Hair

By using a fluorescence-labeled polymer prepared in the above example, adsorptivity for hair of the polymer was evaluated. As a hair model used for the evaluation, keratin powder derived from human was used.

(1) Preparation of Calibration Equation

First, a calibration equation for fluorescence intensity required for calculating adsorptivity for hair was derived. A solution of the fluorescence-labeled polymer prepared in Preparation Example 3 ($1\times10^{-5}$ M, adjusted to pH 7) was used in a test tube with ground-in stopper to obtain the following calibration equation for concentration in solution and fluorescence intensity (Ex. 331 nm, Em. 505 nm).

$$Y=361.223X+112.821, r=0.996$$

(2) Evaluation of Adsorptivity for Hair (i) Non-treated model

Thirty milli-gram keratin powder (derived from human, Tokyo Kasei) was weighed in a test tube with ground-in stopper, added with 5 ml of the sample solution, mixture was stirred for 60 minutes (130 strokes/minute), and centrifuged at 3,000 rpm for 10 minutes. Fluorescence intensity of the supernatant was measured (Ex. 331 nm, Em. 505 nm). Concentration of the supernatant was calculated in accordance with the above calibration equation, and adsorbed amount and adsorptivity were calculated based on the difference from the initial concentration. As a result, the adsorptivity was calculated to be 3.27%.

(ii) Degreased model (damaged hair model)

Thirty milli-gram keratin powder (derived from human, Tokyo Kasei) was weighed in a test tube with ground-in stopper, added with 5 ml of chloroform/methanol=1:1, mixture was stirred for 60 minutes (130 strokes/minute), and centrifuged at 3,000 rpm for 10 minutes, and the supernatant was discarded. Five milli-liter of chloroform/methanol=1:1 was newly added to the residue, and treated similarly. The remained keratin powder was dried by using a vacuum pump for 60 minutes. To this keratin powder, 5 ml of the sample solution was added, stirred for 10 minutes (130 strokes/minute), and centrifuged at 3,000 rpm for 10 minutes. Fluorescence intensity of the supernatant was measured (Ex. 331 nm, Em. 505 nm). Concentration of the supernatant was calculated in accordance with the above calibration equation, and adsorbed amount and adsorptivity were calculated based on the difference from the initial concentration. As a result, the adsorptivity was calculated to be 14.98%.

It was confirmed that, while the amino acid pendant type polymer exhibited adsorptivity also for the non-treated hair, it exhibited stronger adsorptivity for the damaged hair. That is, it was confirmed that the amino acid pendant type polymer of the present invention exhibited protection or improvement effect not only on damaged skin but also on damaged hair. Further, it was confirmed that the group having affinity for amino groups and/or the group having affinity for carboxyl groups, which are the characteristic of the polymers, were more strongly attracted by chemical affinity to portions of disordered hair structures, and restored them.

Industrial Applicability

According to the present invention, there can be provided a polymer which has beneficial effects on skin functions.

According to the present invention, there can also be provided a composition for topical to skin containing a polymer that has a group having affinity for skin and thereby exhibiting beneficial effects on skin functions.

According to the present invention, there can be provided a method for producing compounds represented by Formula (1) with high purity.

According to the present invention, there can be provided a method for protecting or improving skin, which recovers skin structure itself.

According to the present invention, a polymer comprising the compound represented by Formula (3) or a salt thereof as constituent monomers, or a salt thereof can be quantitatively labeled.

What is claimed is:

1. A composition for topical administration to skin or hair comprising a carrier suitable for topical administration to skin or hair and an effective amount of a polymer containing a compound represented by Formula (1) as a constituent monomer, or a salt thereof:

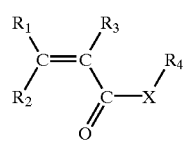

Formula (1)

wherein R1, R2 and R3 each independently represent hydrogen atom, an alkyl group, an alkoxyl group, or an alkylamino group; X-R4 represents an amino acid residue, a polyamine residue, or an aminoalcohol residue; but X represents oxygen atom or a group represented as NH, or a salt thereof.

2. A composition for topical administration to skin or hair comprising a carrier suitable for topical administration to skin or hair and an effective amount of a polymer which has a partial structure represented by Formula (9):

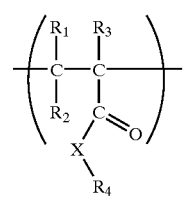

Formula (9)

wherein R1, R2 and R3 each independently represent hydrogen atom, an alkyl group, an alkoxyl group, or an alkylamino group; X-R4 represents an amino acid residue, a polyamine residue, or an aminoalcohol residue; but X represents oxygen atom or a group represented as NH, or a salt thereof.

3. The composition according to claim 2, wherein the partial structure of the polymer represented by Formula (9) is a partial structure represented by Formula (10):

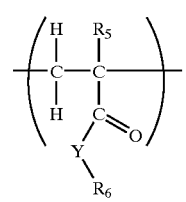

Formula (10)

wherein R5 represents hydrogen atom or methyl group, Y-R6 represents an amino acid residue, a polyamine residue, or an aminoalcohol residue; but Y represents oxygen atom or a group represented as NH.

4. The composition according to claim 3, wherein the partial structure represented by Formula (10) is one or more partial structures selected from partial structures represented by any one of Formulae (11) to (17);

Formula (11)

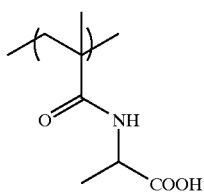

Formula (11)

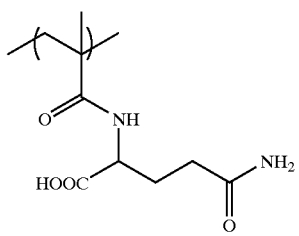

Formula (12)

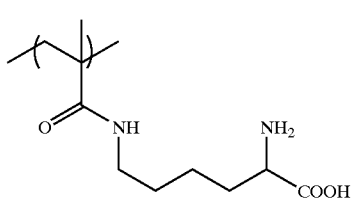

Formula (13)

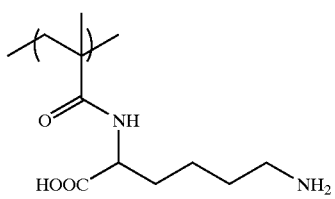

Formula (14)

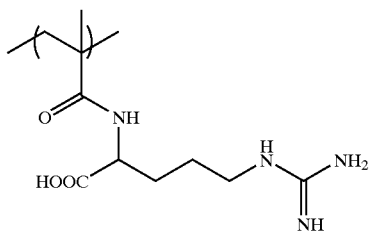

Formula (15)

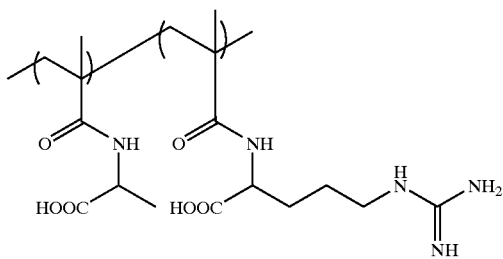

Formula (16)

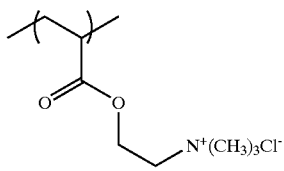

Formula (17)

5. The composition according to claim 1, wherein molecular weight of the polymer is 5000–1,000,000.

6. A method for producing the composition according to claim 1, comprising a step of producing the polymer by polymerizing a compound represented by formula (1) or a salt thereof as a raw material monomer.

7. The composition according to claim 1 or 2, wherein the polymer and/or a salt thereof is a polymer or a salt thereof produced by polymerized only a compound represented by Formula (1) or a salt thereof.

8. The composition according to claim 1 or 2, which is a cosmetic.

9. A method for identifying a group exhibiting affinity for amino acid residues by adsorbing a polymer containing together with one or more compounds represented by Formula (21), and one or more compounds represented by Formula (23):

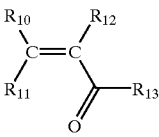

Formula (21)

wherein R10 to R12 each independently represent hydrogen atom or an alkyl group having 1–4 carbon atoms, and R13 represents a group comprising a labeled group, or a salt thereof:

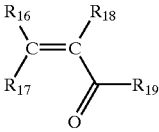

Formula (23)

wherein R16 to R18 each independently represent hydrogen atom or an alkyl group having 1–4 carbon atoms, and R19 represents an amino acid residue or salts thereof, as constituent monomers, or a salt thereof, to said group.

10. The method according to claim 9, wherein the compound represented by Formula (23) is one or more compounds selected from compounds represented by any one of Formulae (3) to (8):

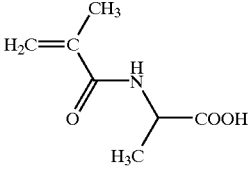

Formula (3)

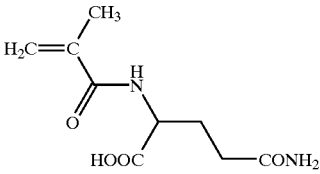

Formula (4)

-continued

Formula (5)

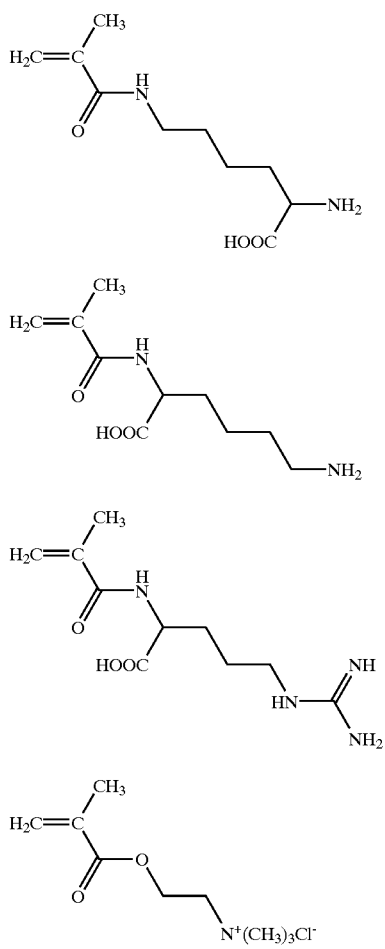

Formula (6)

Formula (7)

Formula (8)

11. A method for differentiating skin, comprising conducting the identification method according to claim 9.

12. The composition according to claim 2, wherein molecular weight of the polymer is 5000–1,000,000.

13. A method for producing the composition according claim 2, comprising a step of producing the polymer by polymerizing a compound represented by Formula (1) or a salt thereof as a raw material monomer.

14. The method according to claim 9, wherein R13 in Formula (21) is a group represented as —NH—$(CH_2)_n$—R14 where n is an integer of 2 to 10, and R14 represents a labeled group.

15. The method according to claim 9, wherein the labeled group is dansyl group.

16. The method according to claim 9, wherein the compound represented by Formula (21) is a compound represented by Formula (22):

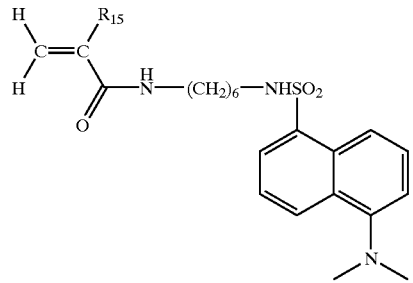

Formula (22)

wherein R15 represents hydrogen atom or methyl group.

* * * * *